(12) United States Patent
Arent

(10) Patent No.: US 9,101,656 B2
(45) Date of Patent: *Aug. 11, 2015

(54) USE OF TEA-DERIVED, THEAFLAVIN ENRICHED EXTRACT TO INCREASE EXERCISE PERFORMANCE AND REDUCE EXERCISE RECOVERY TIME

(71) Applicant: RUTGERS, THE STATE UNIVERSITY OF NEW JERSEY, New Brunswick, NJ (US)

(72) Inventor: Shawn M. Arent, Piscataway, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 103 days.

This patent is subject to a terminal disclaimer.

(21) Appl. No.: 14/059,230

(22) Filed: Oct. 21, 2013

(65) Prior Publication Data

US 2014/0106011 A1    Apr. 17, 2014

Related U.S. Application Data

(62) Division of application No. 12/383,229, filed on Mar. 20, 2009, now Pat. No. 8,563,047.

(60) Provisional application No. 61/070,415, filed on Mar. 21, 2008.

(51) Int. Cl.
    *A01N 65/00*    (2009.01)
    *A61K 36/82*    (2006.01)
    *A23F 3/16*    (2006.01)
    *A23L 1/30*    (2006.01)

(52) U.S. Cl.
    CPC .  *A61K 36/82* (2013.01); *A23F 3/16* (2013.01); *A23L 1/3002* (2013.01)

(58) Field of Classification Search
    CPC ..................................................... A61K 36/00

USPC .......................................................... 424/725
    See application file for complete search history.

(56) References Cited

U.S. PATENT DOCUMENTS

2010/0015254 A1    1/2010  Arent

OTHER PUBLICATIONS

International Search Report and Written Opinion of the International Searching Authority issued by the International Searching Authority in connection with International Application No. PCT/US2009/01768.
Office Action issued Jul. 14, 2010 in connection with U.S. Appl. No. 12/383,229, filed Mar. 20, 2009.
Response to Office Action issued Jul. 14, 2010, filed Aug. 16, 2010, in connection with U.S. Appl. No. 12/383,229, filed Mar. 20, 2009.
Office Action issued Nov. 5, 2010 in connection with U.S. Appl. No. 12/383,229, filed Mar. 20, 2009.
Response to Office Action issued Nov. 5, 2010, filed Mar. 7, 2011, in connection with U.S. Appl. No. 12/383,229, filed Mar. 20, 2009.
Office Action issued May 24, 2011 in connection with U.S. Appl. No. 12/383,229, filed Mar. 20, 2009.
Notice of Appeal filed Nov. 23, 2011 in connection with U.S. Appl. No. 12/383,229, filed Mar. 20, 2009.
Response to Office Action issued May 24, 2012, filed Jun. 22, 2012, in connection with U.S. Appl. No. 12/383,229, filed Mar. 20, 2009.
Office Action issued Oct. 18, 2012 in connection with U.S. Appl. No. 12/383,229, filed Mar. 20, 2009.
Response to Office Action issued Oct. 18, 2012, filed Apr. 13, 2013, in connection with U.S. Appl. No. 12/383,229, filed Mar. 20, 2009.
Notice of Allowance issued Jun. 17, 2013 in connection with U.S. Appl. No. 12/383,229, filed Mar. 20, 2009.

*Primary Examiner* — Michael Meller
(74) *Attorney, Agent, or Firm* — John P. White; Cooper & Dunham LLP

(57) ABSTRACT

This invention provides various methods such as a method for enhancing athletic exercise performance of a subject by administering to the subject a composition comprising a physiologically acceptable carrier and an extract of tea, wherein the extract comprises at least 20% by weight of theaflavins and wherein the composition is administered in an amount effective to enhance the subject's athletic performance.

7 Claims, 17 Drawing Sheets

USE OF TEA-DERIVED, THEAFLAVIN ENRICHED EXTRACT TO INCREASE EXERCISE PERFORMANCE AND REDUCE EXERCISE RECOVERY TIME

This application is a divisional of U.S. Ser. No. 12/383,229, filed Mar. 20, 2009; which claims the benefit of U.S. Provisional Application No. 61/070,415, filed Mar. 21, 2008, the contents of each of which are hereby incorporated by reference in their entirety into this application.

Throughout this application, various U.S. patents and publications are referenced in parentheses by author name and date, or by a patent or patent publication number. Full citations for these publications may be found at the end of the specification immediately preceding the claims. The disclosure of each of these publications in its entirety is hereby incorporated by reference into this application.

BACKGROUND OF THE INVENTION

Recovery after high intensity exercise is becoming increasingly important as sport and exercise become more competitive. After a high-intensity bout of exercise, muscle soreness, including delayed-onset muscle soreness ("DOMS"), decreased power, and decreased performance often follow. DOMS is the muscle soreness that occurs after unaccustomed or high-intensity exercise, most commonly anaerobic (Clarkson & Hubal, 2002). Soreness is usually noted at 24 hours post-exercise and can last any where from five to seven days post-exercise (Clarkson & Hubal, 2002; Feasson et al., 2002; Nosaka & Clarkson, 1996). It has been shown that many high-intensity anaerobic exercises cause DOMS (Lee et al., 2002; McBride et al., 1998; Twist & Eston, 2005). The exact physiological mechanisms responsible for the DOMS resulting from this type of exercise are not agreed upon, though many have been proposed, including changes in osmotic pressure, fluid retention, calcium regulation, and acute inflammation (McArdle, Katch, & Katch, 2001).

Thus there is a need for a supplement that can decrease oxidative stress and inflammation to reduce the magnitude and length of muscle soreness, decreased power and decreased performance so that an athlete may be able to train more frequently, increasing long-term performance. Antioxidant and anti-inflammatory supplements, such as theaflavins found in black tea, have been suggested to decrease oxidative stress and inflammation resulting from physiological stressors such as intense exercise (McKay & Blumberg, 2002; Tomita, Irwin, Xie, & Santoro, 2002) which could help reduce the length and magnitude of post-exercise soreness. This could thus shorten the decrease in strength and performance associated with delayed-onset muscle soreness (DOMS) (Bloomer, Goldfarb, McKenzie, You, & Nguyen, 2004; Clarkson & Thompson, 2000). However, previous research has shown that the effect of anti-inflammatory compounds on DOMS is not currently understood or predictable (Stone et al, 2002; Rice et al, 2008; Dudley, G A, 1999; and McAnulty, et al, 2007)

Catechins, theaflavins and thearubigins are polyphenolic compounds and major components of black tea and oolong tea. Theaflavins and thearubigins are tea-color materials. The approximate mean percentages of these compounds found in black tea beverages are shown in table 1:

TABLE 1

Major components of black tea beverages

| | |
|---|---|
| Catechins | 3-10 |
| Theaflavins | 3-6 |
| Thearubigins | 12-18 |

Components measured in wt % of extract solids.

Theaflavins are a class of benzo[7]annulenone compounds which are formed from oxidation reactions of polyphenolic compounds. There are 12 components in theaflavins, including theaflavin (TF), theaflavin-3-gallate (TFMG), theaflavin-3,3'-digallate (TFdiG) and theaflavin-3'-gallate (TFM'G), which are depicted by the following formula:

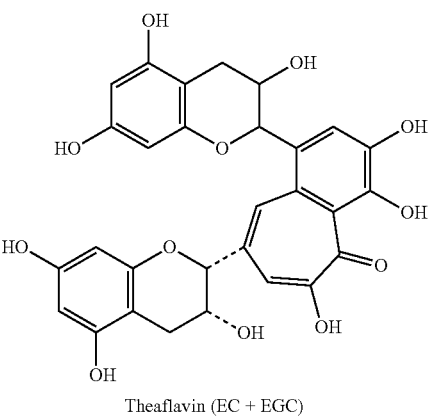

Theaflavin (EC + EGC)

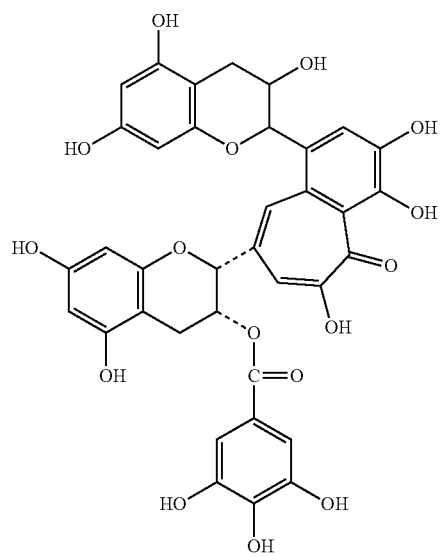

Theaflavin-3-gallate (EC + EGCG)

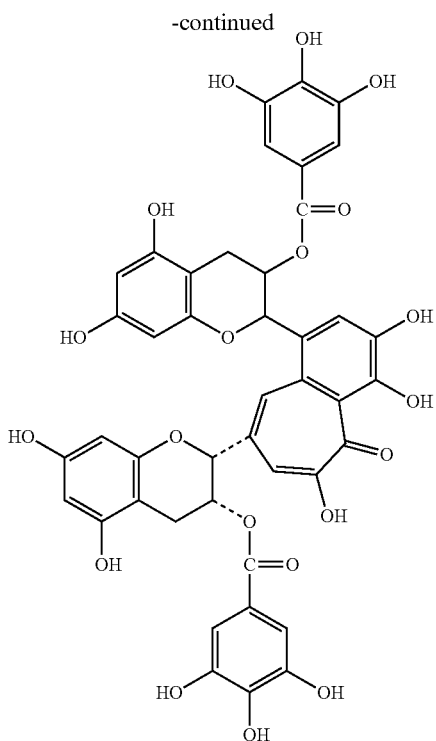

Theaflavin-3,3'-digallate (ECG + EGCG)

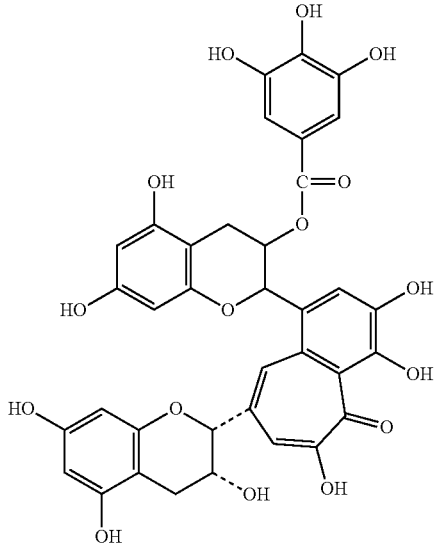

Theaflavin-3'-gallate (ECG + EGC)

which are the four major components. Pure theaflavins are orange colors, form needle crystals, have melting points of 237-240° C., are soluble in water, methanol, ethanol, acetone, n-butanol and ethyl acetate, are slightly soluble in ethyl ether, and are insoluble in chloroform and benzene. Theaflavins in solution are clear orange in color and are slightly acidic with a pH value of about 5.7. The solution color is not affected by the pH of the tea extraction solution, but theaflavins are auto-oxidative in basic solution. The oxidation process increases with the pH value.

Thearubigins are a class of complex, inhomogeneous brown colored phenolic compounds, with a range of molecular weight of $1,000-40 \times 10^3$. Due to inhomogeneity, unclear structure, and unknown properties, it is difficult to isolate and purify the thearubigins.

Tea polyphenols, including catechins and theaflavins, are known for reducing triglyceride, removing free radicals, having anti-oxidant, anti-bacteria, anti-virus, anti-tumor, anti-mutagenic, and odor removal properties, and treating cardiovascular diseases, etc. They are applied in pharmaceutical, nutraceutical and food additive fields.

SUMMARY OF THE INVENTION

This invention provides a method for enhancing athletic exercise performance of a subject which comprises administering to the subject a composition comprising a physiologically acceptable carrier and an extract of tea containing theaflavin-3-gallate and theaflavin-3'-gallate, wherein the extract comprises at least 20% by weight of theaflavins and wherein the composition is administered in an amount effective to enhance the subject's athletic performance.

The invention also provides a method for decreasing recovery time after an exercise session of a subject which comprises administering to the subject a composition comprising a physiologically acceptable carrier and an extract of tea containing theaflavin-3-gallate and theaflavin-3'-gallate, wherein the extract comprises at least 20% by weight of total theaflavin and wherein the composition is administered in an amount effective to decrease recovery time after the subject's exercise session.

The invention also provides a method for enhancing a subject's ability to recover from an exercise session which comprises administering to the subject a composition comprising a physiologically acceptable carrier and an extract of tea containing theaflavin-3-gallate and theaflavin-3'-gallate, wherein the extract comprises at least 20% by weight of total theaflavin and wherein the composition is administered in an amount effective to enhance the subject's ability to recover from the exercise session.

The invention also provides a method for decreasing (the effects of) exercise-induced, delayed onset, muscle soreness in a subject which comprises administering to the subject a composition comprising a physiologically acceptable carrier or excipient and an extract of tea containing theaflavin-3-gallate and theaflavin-3'-gallate, wherein the extract comprises at least 20% by weight of total theaflavin and wherein the composition is administered in an amount effective to decrease (the effects of) delayed onset, muscle soreness in the subject.

The invention also provides a method for decreasing exercise-induced, acute inflammation in a subject which comprises administering to the subject a composition comprising a physiologically acceptable carrier and an extract of tea containing theaflavin-3-gallate and theaflavin-3'-gallate, wherein the extract comprises at least 20% by weight of total theaflavin and wherein the composition is administered in an amount effective to decrease acute inflammation in the subject.

The invention also provides a method of treating or preventing chronic heart failure in a subject which comprises administering to the subject a composition comprising a physiologically acceptable carrier and an extract of tea containing theaflavin-3-gallate and theaflavin-3'-gallate, wherein the extract comprises at least 20% by weight of total theaflavin and wherein the composition is administered in an amount effective to permit the subject to exercise more frequently with less soreness so as to stimulate cardiac health in the subject and thereby treat or prevent chronic heart failure in the subject.

The invention also provides a method for increasing a subject's resistance to exercise-induced performance losses which comprises administering to the subject a composition comprising a physiologically acceptable carrier and an extract of tea containing theaflavin-3-gallate and theaflavin-3'-gallate, wherein the extract comprises at least 20% by weight of total theaflavin and wherein the composition is administered in an amount effective to raise the subject's baseline level of glutathione and thereby increase the subject's resistance to exercise-induced performance losses.

The invention also provides a method of preventing exercise-induced muscle cell degradation in a subject which comprises administering to the subject a composition comprising a physiologically acceptable carrier and an extract of tea containing theaflavin-3-gallate and theaflavin-3'-gallate, wherein the extract comprises at least 20% by weight of total theaflavin and wherein the composition is administered in an amount effective to diminish degradation of muscle cell membranes caused by exercise and thereby prevents exercise-induced cell degradation in the subject.

The invention also provides a method for enhancing a subject's ability to maintain a high level of performance in the presence of elevated levels of lactic acid which comprises administering to the subject a composition comprising a physiologically acceptable carrier and an extract of tea containing theaflavin-3-gallate and theaflavin-3'-gallate, wherein the extract comprises at least 20% by weight of total theaflavin and wherein the composition is administered in an amount effective to enhance the subject's ability to maintain a high level of performance in the presence of elevated levels of lactic acid.

The invention also provides a method for enhancing a positive response to physical therapy in a subject which comprises administering to the subject a composition comprising a physiologically acceptable carrier and an extract of tea containing theaflavin-3-gallate and theaflavin-3'-gallate, wherein the extract comprises at least 20% by weight of total theaflavin and wherein the composition is administered in an amount effective to enhance the subject's response to physical therapy.

The invention also provides a method for maintaining a subject's flexibility after exercise which comprises administering to the subject a composition comprising a physiologically acceptable carrier and an extract of tea containing theaflavin-3-gallate and theaflavin-3'-gallate, wherein the extract comprises at least 20% by weight of total theaflavin and wherein the composition is administered in an amount effective to maintain a subject's flexibility after exercise.

This invention also provides a method for enhancing athletic exercise power and performance of a subject which comprises administering to the subject a composition comprising a physiologically acceptable carrier or excipient and an extract of tea containing theaflavin-3-gallate and theaflavin-3'-gallate, wherein the extract comprises at least 10% by weight of total theaflavin and wherein the composition is administered in an amount effective to enhance the subject's athletic power and performance.

DETAILED DESCRIPTION OF THE INVENTION

Figure 1:
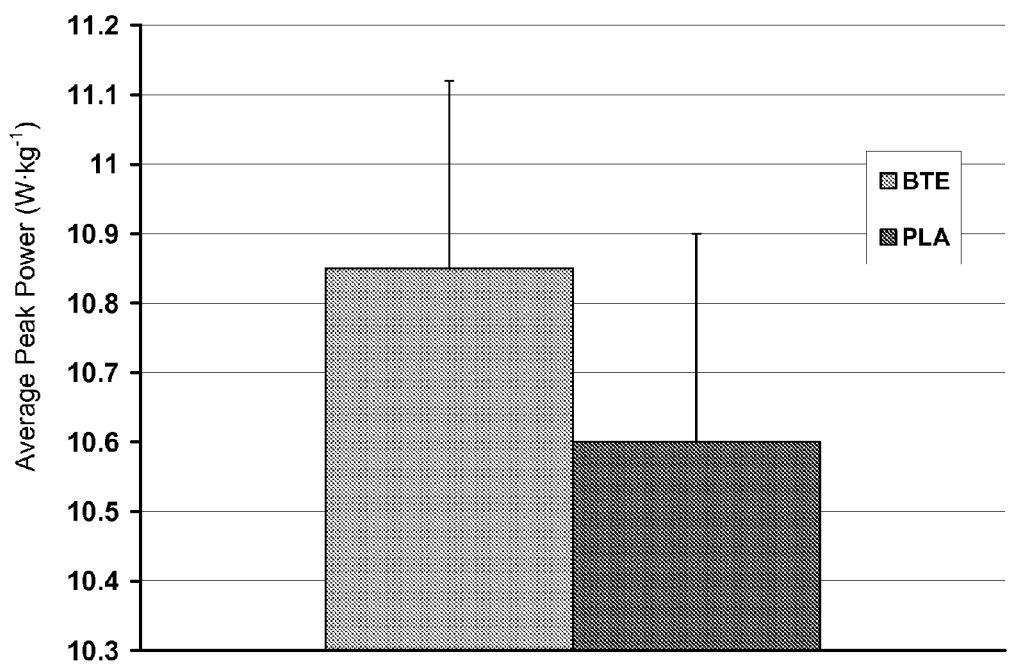
FIG. 1 shows the effects of BTE vs PLA supplementation on average peak power across WAnT and eight 10 s intervals.

For convenience, before further description of the present invention, certain terms employed in the specification, examples and appended claims are defined here.

A "subject" means any organism including, without limitation, a mammal such as a cat, a dog, a horse, a camel, and a primate (human or non-human). In the preferred embodiment, the subject is a human being.

An "effective amount" of a composition means an amount of the composition sufficient to cause the desired result in a given subject. The effective amount will vary from subject to subject and depending on the condition to be treated, the agent delivered, and the route of delivery. A person of ordinary skill in the art can perform routine titration experiments to determine such an amount. Depending upon the agent delivered, the effective amount of a composition can be delivered continuously, such as by a suppository, or at periodic intervals (for example, on one or more separate occasions). Desired time intervals of multiple amounts of a particular agent can be determined without undue experimentation by one skilled in the art. The invention provides for an effective amount of a theaflavin-enriched extract of tea from about 50 mg of the extract to about 1000 mg of the extract per day. The invention also provides for administering the theaflavin-enriched extract with a food and/or beverage in an amount of about 44 mg ten times per day. The invention also provides for an effective amount of theaflavin-enriched extract in the amount of about 440 mg per day. The invention also provides for an effective amount of extract in the amount of about 880 mg per day. The invention also provides for an effective amount of a theaflavin-enriched extract of tea providing from about 50 mg to about 2600 mg of total theaflavins per day. The invention also provides for an effective amount of a theaflavin-enriched extract of tea providing from about 300 mg to about 1000 mg of total theaflavins per day. The invention also provides for an effective amount of tea extract providing about 175 mg of total theaflavins per day. The invention also provides for an effective amount of tea extract providing about 350 mg of total theaflavins per day. The invention also provides for an effective amount of tea extract providing about 525 mg of total theaflavins per day.

The term "food" includes all edible compositions regardless of form and thus includes gels, gel packs, liquids, syrups, and/or solids.

The term "free of ethyl acetate" means that there is no trace of ethyl acetate. In contrast a composition that comprises an ethyl acetate extract, would contain traces of ethyl acetate and therefore is not "free of ethyl acetate" as used herein.

The term "percent by weight" of a theaflavin or theaflavins means the weight of such theaflavin or theaflavins as measured by high-performance liquid chromatography (HPLC), sometimes referred to as high-pressure liquid chromatography. While it is also possible to measure the percent by weight of theaflavins by using UV absorption techniques, such techniques detect ancillary materials and therefore report a higher and inaccurate percentage by weight of theaflavins than the HPLC method of measurement. Therefore, to provide the most accurate disclosure, all measurements and reporting of percentages by weight are done using HPLC.

The term "increased performance" of a subject refers to an increase in the subject's mean peak power and/or an increase in the subject's mean average power over the course of several exercise intervals. Accordingly, a subject can experience "increased performance" even if the subject's peak power and/or mean power did not increase during any given exercise interval.

"Administering" a composition can be effected or performed using any of the various methods and delivery systems known to those skilled in the art. The following non-limiting examples are provided to further illustrate the claimed invention. Compositions comprising tea extract can be formulated for administration as a food supplement using one or more fillers. Alternatively, compositions comprising these extracts can be administered as conventional pharmaceuticals using one or more physiologically acceptable carriers or excipients. Nutraceutical compositions can be formulated for administration by any route including, but not limited to, inhalation or insufflation (through mouth or nose), oral, buccal, parenteral, vaginal, or rectal administration. In one embodiment, oral administration, the compositions are added directly to foods and ingested as part of a normal meal. Compositions for use in the present invention can also be administered in the form of tablets or capsules prepared by conventional means with pharmaceutically acceptable excipients such as binding agents, fillers, lubricants, disintegrants, or wetting agents. Examples of specific compounds for use in formulating tablets and capsules are described in detail in the U.S. Pharmacopeia. Tablets comprising the extract can also be coated by methods well known in the art. Liquid preparations for oral administration can also be used. Liquid preparations can be in the form of solutions, syrups, or suspensions, or a dry product for reconstitution with water or another suitable vehicle before use. Such liquid preparations can be prepared by conventional means with pharmaceutically acceptable additives such as suspending agents, emulsifying agents, non-aqueous vehicles, and preservatives. Again, specific additives are well known to those of skill and are listed in places such as the U.S. Pharmacopeia. In one embodiment, the oral preparation is formulated to provide controlled time release of the active nutraceutical components. For buccal administration, the extract can be formulated as a tablet or lozenge.

For administration by inhalation, compositions for use in the present invention can be delivered in the form of an aerosol spray in a pressurized package or as a nebulizer, with use of suitable propellants. In the case of a pressurized aerosol, the dosage unit can be determined by providing a valve to deliver a metered dose.

Parenterally administered compositions are formulated to allow for injection, either as a bolus or as a continuous infusion. Formulations for injection can be prepared in unit dosage forms, such as ampules, or in multi-dose units, with added preservatives. The compositions for injection can be in the form of suspensions, solutions, or emulsions, in either oily or aqueous vehicles. They may also contain formulatory agents such as suspending agents, stabilizing agents, and/or dispersing agents. The active ingredient may also be presented in powder form for reconstitution with a suitable vehicle before use. Specific examples of formulating agents for parenteral injection are found in the U.S. Pharmacopeia.

For rectal administration or vaginal administration, compositions for use in one of the present invention can be formulated as suppositories, creams, gels, or retention enemas. As one skilled in the art would recognize, suppositories may avoid first pass metabolism.

For dietary supplements, the extract can be added in concentrations up to 5% by weight and mixed according to methods routine in the art. Dietary supplements for animals can be prepared in a variety of forms including, but not limited to, liquid, powder, or solid pill forms. In the present invention, tea extract can be administered either alone or in combination with other phytochemicals known to enhance athletic performance and/or decrease recovery time, where combining compounds or extracts would lead to synergistic effects.

Thus the invention provides a method for enhancing athletic exercise performance of a subject which comprises administering to the subject a composition comprising a physiologically acceptable carrier and an extract of tea, wherein the extract comprises at least 20% by weight of theaflavins and wherein the composition is administered in an amount effective to enhance the subject's athletic performance.

The extract used in the method for enhancing athletic exercise performance may comprise at least either 2% theaflavin (TF-1), 7% theaflavin-3-gallate, 2% theaflavin-3'-gallate and/or 5% theaflavin-3,3'-digallate by weight.

The extract used in the method for enhancing athletic exercise performance may comprise from about 12 to about 17% by weight theaflavin-3-gallate and from about 3% to about 8% theaflavin-3'-gallate.

The extract used in the method for enhancing athletic exercise performance may comprise from about 12 to about 17% by weight theaflavin-3-gallate, from about 3% to about 8% theaflavin-3'-gallate and from about 9% to about 14% by weight theaflavin-3,3'-digallate.

The extract used in the method for enhancing athletic performance may comprise a combined at least 15% by weight of theaflavin-3-gallate and theaflavin-3'-gallate.

The extract used in the method for enhancing athletic exercise performance may be an ethanol extract of tea. The extract used in the method for enhancing athletic exercise performance may also be an ethyl acetate extract, membrane filtrate, and/or supercritical $CO_2$ extract of tea.

The extract used in the method for enhancing athletic exercise performance may be a black tea extract. The extract used in the method for enhancing athletic exercise performance may also be an oolong tea extract.

The composition used in the method for enhancing athletic exercise performance may be administered orally. The composition used in the method for enhancing athletic exercise performance may also be administered topically or as a suppository.

The carrier used in the method for enhancing athletic exercise performance may be a food product. The carrier used in the method for enhancing athletic exercise performance may be a beverage, a dietary supplement, a capsule, a tablet, a lozenge, a coated tablet, a solution, a syrup, or a suspension.

The composition used in the method for enhancing athletic exercise performance may comprise about 440 mg of the extract and may be administered twice per day. The composition used in the method for enhancing athletic exercise performance may comprise from about 50 mg to about 1000 mg of the extract and may be administered between 4 and 10 times per day. The composition used in the method for enhancing athletic exercise performance may comprise about 175 mg of total theaflavins and may be administered twice per day.

The composition used in the method for enhancing athletic exercise performance may comprise not more than 2% by weight of caffeine.

The invention also provides a method for decreasing recovery time after an exercise session of a subject which comprises administering to the subject a composition comprising a physiologically acceptable carrier and an extract of tea, wherein the extract comprises at least 20% by weight of total theaflavin and wherein the composition is administered in an amount effective to decrease recovery time after the subject's exercise session. This method for decreasing recovery time after an exercise session may use any of the extracts, carriers or compositions described above for use in the method of enhancing athletic exercise performance.

The invention also provides a method for enhancing a subject's ability to recover from an exercise session which comprises administering to the subject a composition comprising a physiologically acceptable carrier and an extract of tea, wherein the extract comprises at least 20% by weight of total theaflavin and wherein the composition is administered in an amount effective to enhance the subject's ability to recover from the exercise session. This method for enhancing a subject's ability to recover from an exercise session may use any of the extracts, carriers or compositions described above for use in the method of enhancing athletic exercise performance.

The invention also provides a method for decreasing (the effects of) exercise-induced, delayed onset, muscle soreness in a subject which comprises administering to the subject a composition comprising a physiologically acceptable carrier or excipient and an extract of tea, wherein the extract comprises at least 20% by weight of total theaflavin and wherein the composition is administered in an amount effective to decrease (the effects of) delayed onset, muscle soreness in the subject. This method for decreasing exercise-induced, delayed onset, muscle soreness may use any of the extracts, carriers or compositions described above for use in the method of enhancing athletic exercise performance.

The invention also provides a method for decreasing exercise-induced, acute inflammation in a subject which comprises administering to the subject a composition comprising a physiologically acceptable carrier and an extract of tea, wherein the extract comprises at least 20% by weight of total theaflavin and wherein the composition is administered in an amount effective to decrease acute inflammation in the subject. This method for decreasing exercise-induced, acute inflammation may use any of the extracts, carriers or compositions described above for use in the method of enhancing athletic exercise performance.

The invention also provides a method of treating or preventing chronic heart failure in a subject which comprises administering to the subject a composition comprising a physiologically acceptable carrier and an extract of tea, wherein the extract comprises at least 20% by weight of total theaflavin and wherein the composition is administered in an amount effective to permit the subject to exercise more frequently with less soreness so as to stimulate cardiac health in the subject and thereby treat or prevent chronic heart failure in the subject. This method for treating or preventing chronic heart failure may use any of the extracts, carriers or compositions described above for use in the method of enhancing athletic exercise performance.

The invention also provides a method for increasing a subject's resistance to exercise-induced performance losses which comprises administering to the subject a composition comprising a physiologically acceptable carrier and an extract of tea, wherein the extract comprises at least 20% by weight of total theaflavin and wherein the composition is administered in an amount effective to raise the subject's baseline level of glutathione and thereby increase the subject's resistance to exercise-induced performance losses. This method for increasing a subject's resistance to exercise-induced performance losses may use any of the extracts, carriers or compositions described above for use in the method of enhancing athletic exercise performance.

The invention also provides a method of preventing exercise-induced muscle cell degradation in a subject which comprises administering to the subject a composition comprising a physiologically acceptable carrier and an extract of tea, wherein the extract comprises at least 20% by weight of total theaflavin and wherein the composition is administered in an amount effective to diminish degradation of muscle cell membranes caused by exercise and thereby prevents exercise-induced cell degradation in the subject. This method for preventing exercise-induced muscle cell degradation may use any of the extracts, carriers or compositions described above for use in the method of enhancing athletic exercise performance.

The invention also provides a method for enhancing a subject's ability to maintain a high level of performance in the presence of elevated levels of lactic acid which comprises administering to the subject a composition comprising a physiologically acceptable carrier and an extract of tea, wherein the extract comprises at least 20% by weight of total theaflavin and wherein the composition is administered in an amount effective to enhance the subject's ability to maintain a high level of performance in the presence of elevated levels of lactic acid. This method for enhancing a subject's ability to maintain a high level of performance in the presence of elevated levels of lactic acid may use any of the extracts, carriers or compositions described above for use in the method of enhancing athletic exercise performance.

The invention also provides a method for enhancing a positive response to physical therapy in a subject which comprises administering to the subject a composition comprising a physiologically acceptable carrier and an extract of tea, wherein the extract comprises at least 20% by weight of total theaflavin and wherein the composition is administered in an amount effective to enhance the subject's response to physical therapy. This method for enhancing a positive response to physical therapy may use any of the extracts, carriers or compositions described above for use in the method of enhancing athletic exercise performance.

The invention also provides a method for maintaining a subject's flexibility after exercise which comprises administering to the subject a composition comprising a physiologically acceptable carrier and an extract of tea, wherein the extract comprises at least 20% by weight of total theaflavin and wherein the composition is administered in an amount effective to maintain a subject's flexibility after exercise. This method for maintaining a subject's flexibility after exercise may use any of the extracts, carriers or compositions described above for use in the method of enhancing athletic exercise performance.

This invention also provides a method for enhancing athletic exercise power and performance of a subject which comprises administering to the subject a composition comprising a physiologically acceptable carrier or excipient and an extract of tea, wherein the extract comprises at least 10% by weight of total theaflavin and wherein the composition is administered in an amount effective to enhance the subject's athletic power and performance. This method for enhancing athletic exercise power and performance may use any of the extracts, carriers or compositions described above for use in the method of enhancing athletic exercise performance.

Examples of tea extracts suitable for use in the methods of this invention include, but are not limited to, the extracts disclosed in U.S. Pat. Nos. 7,157,493; 7,238,376; 7,087,790; and 5,532,012, and published PCT application WO 2009/014758 the contents of each of which is hereby incorporated by reference into this application.

The extract disclosed in U.S. Pat. No. 7,157,493 is made by fermenting green tea to form a mixture of theaflavin, theaflavin-3-gallate, theaflavin-3'-gallate and theaflavin-3,3'-digallate, which are then extracted from the mixture by contacting them with organic solvent, such as ethyl acetate. In one embodiment it provides a mixture of theaflavins that is greater than 95% pure and contains between about 40% and about 50% theaflavin, between about 15% and about 25% of theaflavin-3-gallate, between about 10% and about 14% theaflavin-3'-gallate and between about 15% and about 25% of theaflavin-3,3'-digallate. In another embodiment, the mixture of theaflavins is comprised of about 47% theaflavin, about 19% of theaflavin-3-gallate, about 14% theaflavin-3'-gallate and about 20% of theaflavin-3,3'-digallate. In yet another embodiment, the theaflavin mixture is resolved into theaflavin, theaflavin-3-gallate, theaflavin-3'-gallate and theaflavin-3,3'-digallate.

The extract disclosed in U.S. Pat. No. 7,238,376 is made by extracting theaflavins from black tea with ethyl acetate to form a mixture of theaflavin-3-gallate and theaflavin 3'-gallate. In one embodiment, theaflavin-3-gallate and theaflavin-3'-gallate are present in a total concentration of up to 5% of the composition. In another embodiment, the theaflavin-3-gallate and theaflavin-3'-gallate are present in a total concentration of between 50 µM and 100 µM in the composition.

The extract disclosed in U.S. Pat. No. 7,087,790 is made by subjecting specific green tea polyphenols to enzymatic oxidation methods to independently synthesize theaflavin, theaflavin-3-gallate, theaflavin-3'-gallate, and theaflavin-3,3'-digallate.

The extract disclosed in U.S. Pat. No. 5,532,012 is made by extracting black tea with water, concentrating the solution into a tea cream, and extracting theaflavins from the solution with an organic liquid. In one embodiment, the mixture contains about 21.37% by weight of theaflavins. In another embodiment, the mixture contains about 3.55% theaflavin, about 5.95% theaflavin-3-gallate, about 3.75% theaflavin-3'-gallate, and about 8.14% theaflavin-3,3'-digallate.

The extract disclosed in published PCT application WO 2009/014758 is a theaflavin enriched extract of tea comprising at least 10% by weight of total theaflavins and having a low content of high molecular weight thearubigins. Disclosed methods include extracting theaflavins from tea using ethanol to produce an extract free of ethyl acetate and optionally fermenting the tea in a tank containing water and fruit or vegetable juice before extraction. This method provides a composition that may comprise from about 12% to about 17% by weight theaflavin-3-gallate, from about 3% to about 8% theaflavin-3'-gallate and/or from about 9% to about 14% by weight theaflavin-3,3'-digallate.

The molecular structure of theaflavin (TF-1); theaflavin-3-gallate; theaflavin-3'-gallate; and theaflavin-3,3'-digallate are well known in the art and are disclosed in U.S. Pat. No. 7,157,493, the contents of which is hereby incorporated by reference into this application.

The following Examples are set forth to aid in an understanding of the subject matter of this disclosure, but are not intended to, and should not be construed to, limit in any way the claims which follow thereafter.

Example 1

Synopsis of the Clinical Study

Recovery after high intensity exercise is becoming increasingly important as sport and exercise become more competitive. After a high-intensity bout of exercise, muscle soreness, decreased power, and decreased performance often follow. By reducing the magnitude and length of these effects, an athlete may be able to train more frequently, increasing long-term performance. The purpose of this study was to examine the impact of supplementing with a theaflavin-enriched black tea extract (BTE) on delayed onset muscle soreness (DOMS), performance, inflammation, oxidative stress, and Cortisol responses to a high-intensity anaerobic exercise protocol. Theaflavins have demonstrated anti-inflammatory properties and there is both in vivo and in vitro evidence that this particular BTE (WG0401; WellGen, New Brunswick, N.J.) influences pro-inflammatory cytokine and COX-2 gene expression. This has potential application for recovery from high-intensity exercise, particularly if using repeated anaerobic intervals. Given the interrelated nature of pro-inflammatory cytokine production, HPA axis activation, and formation of reactive oxygen species (ROS), it was hypothesized that BTE would improve recovery from an acute bout of intense exercise. Additionally, it was predicted that the enhanced recovery and reduced inflammation would positively influence the ratings of DOMS at 24 and 48 hours post-exercise.

A total of 18 college-age males with 1+ years of weight training experience (at least 3 days per week) completed all stages of data collection. This study was limited to males in order to control for fluctuations in cytokines and cortisol that occur during the menstrual cycle and because of power differences between genders. Based on self-report and capsule count from each returned supplement bottle, it appears that 100% compliance was achieved with all 18 subjects. A double-blind, crossover design was used for this clinical trial. Each subject completed a familiarization session to control for practice effects on the anaerobic test and two separate testing sessions (T1 and T2). During T1 and T2, blood samples were obtained before, immediately after, and 30 and 60 min after a Wingate Anaerobic Test (WAnT) for later analysis of oxidative stress markers (8-iso $PGF_{2\alpha}$ [8-isoprostane], total and oxidized glutathione [TGSH and GSSG]), muscle breakdown (creatine kinase [CK]), Cortisol (CORT), and inflammatory cytokines (interleukin-1b [IL-1b], IL-2, IL-4, IL-6, IL-10, IL-12p40, and IFN-y). Additionally, capillary blood samples were analyzed during each test in order to assess blood lactate accumulation and recovery. Participants were asked to rate perceived muscle soreness at 24 and 48 hours post using a visual analog scale.

Following the familiarization session, subjects were randomly assigned to order of administration of the theaflavin-enriched BTE (WG0401; WellGen, Inc., New Brunswick, N.J.) and a placebo (PLA). Bottles of the BTE and PLA were provided in a blinded fashion by WellGen, Inc., with a decoding list secured from the investigators until the completion of the assays. Subjects were instructed to take two capsules in the morning and two in the early afternoon. Each 2-capsule serving of the experimental product contains ~440 mg BTE and is standardized for 175 mg TF. Placebo was matched for appearance. Subjects consumed the BTE or PLA for 9 days. T1 occurred on day 7 and administration continued for 2 more days during the assessment of DOMS. Each subject then underwent a 5-day washout before beginning the 9-day administration period of whichever product they did not receive in the initial supplementation phase. As with the first phase, T2 occurred on day 7 of the second phase and administration continued for an additional 2 days during the assessment of DOMS. On each testing day, subjects performed a 30 s WAnT followed by 5 min of recovery and then eight 10 s intervals of all-out cycling. Each interval was separated by 2 min of recovery. The resistance for the WAnT and intervals was set at 0.10 kp/kg body weight. Due to the exploratory nature of this study, significance was set at a <0.10 for all analyses.

Analysis of the WAnT performance data indicated that across the 30 s WAnT and all eight 10 s intervals, BTE resulted in significantly higher average peak power and average mean power compared to PLA. Both conditions resulted in significant post-exercise elevations in LAC, though the values were significantly higher for BTE at 0 and 5 min post. Combined with the higher power outputs, this also indicates that the BTE group did more total work during the protocol, which makes the following muscle soreness and biochemical results that much more remarkable.

Across the 48 h post-exercise period, BTE resulted in significantly lower DOMS ratings compared to PLA. Both groups displayed significant elevations in CK post-exercise. However, the CK response did not return to baseline until 60 min post in PLA while BTE had recovered to baseline values by 30 min post and had significantly lower CK compared to PLA at the 30 min post-exercise assessment. Analysis of the oxidative stress-related variables indicated significantly higher resting GSH in the BTE condition, which is an indicator of antioxidant status. There were equivalent GSSG responses immediately post-exercise, but the recovery from the oxidative stress was significantly more pronounced in the BTE condition with significantly lower GSSG levels in BTE by 30 min post and persisting through the 60 min follow-up compared to PLA. AUC analysis indicated significantly lower total GSSG in the BTE over the assessment period. The GSH:GSSG ratio analyses indicated significantly higher ratios for the BTE at 30 and 60 min post compared to PLA. A lower/decreasing ratio indicates greater overall oxidative stress as GSSG is prevented from reconverting to GSH. The AUC analysis for the GSH:GSSG ratio was also significant, with an overall greater ratio seen for the BTE condition. Both conditions also had significant elevations in 8-iso following exercise. Though there was not a significant interaction effect, AUC analysis revealed significant differences, with lower overall 8-iso secretion in the BTE condition thus indicating lower total oxidative stress. Consistent with the oxidative stress findings, analysis of CORT response revealed significantly lower overall CORT secretion for BTE as evidenced by a significant Condition effect and a significant difference in AUC. It appears as though hypothalamic-pituitary-adrenal (HPA) axis recovery is more pronounced in BTE or that HPA activation was not as pronounced to begin with.

Analyses of the cytokine responses indicated that there were significant Time main effects for IL-2, IL-4, IL-6, IL-10, IL-12p40, and IFNy. For all of the cytokines, there were increases across conditions immediately post-exercise. This is also an indication of how stressful this particular protocol was. Graphic trends suggest that these responses were typically more pronounced in PLA, particularly for IL-1, IL-4, IL-6, and IL-12p40. AUC analyses indicated significantly greater overall secretion of IL-4 and IL-12p40 in PLA compared to BTE. Overall, the cytokine analyses and graphic trends, coupled with the differences in oxidative stress and HPA activation, present a cohesive picture of superiority of BTE over PLA for blunting these physiological responses or for speeding recovery following exercise. This is further reflected in the DOMS results. One of the most important considerations in all of this is the fact that these biochemical and DOMS responses were superior with BTE supplementation despite the fact that the BTE condition resulted in greater overall total work during anaerobic interval training. It is also important to recognize that BTE did not prevent these physiological responses, which is an important consideration for fuel mobilization and induction of training effects. In fact, research has demonstrated the importance of a certain degree of inflammation and HPA activation to maximize performance and adaptations to chronic training. BTE appears to blunt some of these physiological responses or enhance their recovery and re-establishment of homeostasis following intense exercise. This would still allow for optimization of performance during an acute bout of exercise while also speeding the recovery process in order to facilitate engaging in future acute bouts of training without dealing with residual muscle damage from previous work.

Background of the Clinical Study

Recovery after high intensity exercise is becoming increasingly important as sport and exercise become more competitive. After a high-intensity bout of exercise, muscle soreness, decreased power, and decreased performance often follow. By reducing the magnitude and length of these effects, an athlete may be able to train more frequently, increasing long-term performance. Antioxidant and anti-inflammatory supplements, such as theaflavins found in black tea, have been suggested to decrease oxidative stress and inflammation resulting from physiological stressors such as intense exercise (McKay & Blumberg, 2002; Tomita, Irwin, Xie, & Santoro, 2002) which could help reduce the length and magnitude of post-exercise soreness. This could thus shorten the decrease in strength and performance associated with delayed-onset muscle soreness ("DOMS") (Bloomer, Goldfarb, McKenzie, You, & Nguyen, 2004; Clarkson & Thompson, 2000).

DOMS is the muscle soreness that occurs after unaccustomed or high-intensity exercise, most commonly anaerobic (Clarkson & Hubal, 2002). Soreness is usually noted at 24 hours post-exercise and can last anywhere from five to seven days post-exercise (Clarkson & Hubal, 2002; Feasson et al., 2002; Nosaka & Clarkson, 1996). It has been shown that many high-intensity anaerobic exercises cause DOMS (Lee et al., 2002; McBride et al., 1998; Twist & Eston, 2005). One such exercise suggested to induce muscle soreness is the Wingate anaerobic test (WAnT) (Guevas et al., 2005; Meyer, Gabriel, Ratz, Miiller, &Kindermann, 2001). The physiological stress associated with the typical 30 s or 60 s WAnT can even be further increased by adding multiple shorter (i.e., 10 s) intervals to the protocol (Meyer et al., 2001). The exact physiological mechanisms responsible for the DOMS resulting from this type of exercise are not agreed upon, though many have been proposed, including changes in osmotic pressure, fluid retention, calcium regulation, and acute inflammation (McArdle, Katch, & Katch, 2001).

Although several models of DOMS have been suggested, each acknowledges damage to the working muscle tissue as a necessary event. In the most commonly accepted hypothesis, muscle damage is the beginning of a chain of events ending with DOMS (Clarkson & Hubal, 2002; Malm, 2001; Nosaka & Clarkson, 1996; Tidball, 2005). As the muscle is exposed to high-intensity anaerobic exercise, the sarcolemma becomes damaged and the muscle is "damaged" through catabolic hormones secreted due to activation of the hypothalamic-pituitary-adrenal (HPA) axis. This allows myoglobin and cytosolic enzymes such as creatine kinase (CK), which are naturally found inside a muscle cell, to "leak" into the blood (McArdle, Katch, & Katch, 2001). This protein is commonly used as an indirect marker of muscle damage due to its large increase with anaerobic exercise (Clarkson & Hubal, 2002). As CK leaks out of the cell, calcium begins to accumulate, further increasing damage to the cell (McArdle, Katch, & Katch, 2001). Local blood flow is increased and neutrophils invade the damaged area, which also serves to increase the release of free oxygen radicals or reactive oxygen species (ROS). This excessive increase in ROS leads to oxidative stress and possibly more cell damage (Clarkson & Hubal, 2002; MacIntyre, Sorichter, Mair, Berg, & McKenzie, 2001; Vassilakopoulos et al., 2003). According to Goldfarb, Bloomer, and McKenzie (2005), high intensity exercise can destroy heme proteins, which in turn can increase ROS such as $H_2O_2$. These then interact with transition metals found in the body to form free radicals (Clarkson & Thompson, 2000).

One of the main side effects of ROS production is lipid peroxidation. Cell membranes are very susceptible to these processes because of the many unsaturated points along their backbone (Clarkson & Thompson, 2000). When lipid peroxidation occurs in the cell membrane it increases damage by increasing fluidity and deactivating some of the receptors and enzymes located in these cell membranes, disrupting homeostasis in the cell (Clarkson & Thompson, 2000). By testing the byproducts of this process it is possible to estimate the extent to which oxidative stress is occurring and if it is in turn related to muscle damage and DOMS.

There are numerous byproducts, or biomarkers, that can be indicative of lipid peroxidation and oxidative stress. Because we are measuring markers of lipid peroxidation and not measuring ROS directly, it is suggested that more than one marker be used. Glutathione (GSH) is a commonly used biomarker of oxidative stress. When $H_2O_2$ is present it oxidizes to glutathione disulfide (GSSG). If oxidative stress is severe enough, the ratio of GSSG:GSH will remain heightened. If not, GSSG will be rapidly reduced back to its original form of GSH(Clarkson & Thompson, 2000). One study examined the response of GSSG:GSH to a 30 s WAnT and found a significant increase at 0, 15, 60, and 120 min post-exercise (Guevas et al., 2005). Another common biomarker of oxidative stress is F2-isoprostane (specifically, 8-isoprostane). These are thought to be some of the most reliable biomarkers due to their sensitivity (Basu, 2003). F2-isoprostanes are synthesized from polyunsaturated fatty acids (PUFA), and catalyzed by free radicals. F2-isoprostane marks tissue oxidation in the lungs, kidney, brain, and muscle. Childs et al. (2001) examined the response of 8-isoprostane to a high-intensity anaerobic exercise protocol of three sets of 10 eccentric arm curls at 80% of a 1RM, which resulted in severe DOMS for several days post-exercise. 8-isoprostane was significantly higher than baseline for three days post exercise and remained elevated until day seven, suggesting an increase in oxidative stress (Childs et al., 2001). Although no studies to date have examined the effects of the WAnT on 8-isoprostane production, previous studies show 8-isoprostane as a reliable marker of oxidative stress in other high intensity anaerobic exercises. WAnT, however, has been shown to increase other markers of oxidative stress such as electron spin resonance (ESR) and malondialdehyde (MDA) (Baker et al, 2004; Groussard et al., 2003).

It has been suggested that the ROS leading to oxidative stress stimulate a production of pro-inflammatory cytokines eventually leading to DOMS (Reid & Li, 2001; Vassilakopoulos, 2003). Cytokines are proteins that regulate the flux of inflammatory cells causing either an increase or decrease to an area. As pro-inflammatory cytokines such as interleukin (IL)-1β, IL-2, IL-6, IL-8 and IFNy are released in response to exercise induced oxidative stress, acute inflammation occurs (Clarkson & Hubal, 2002; Willoughby, McFarlin, & Bois, 2003). This process is necessary for healing of the muscle cell, as it allows for increasing amounts of neutrophils to accumulate in the area, thus providing for phagocytosis of debris in the area of damage (Tidball, 2005). Although some degree of swelling in the muscle is necessary, excessive inflammation is thought to be one of the major direct causes of DOMS. As the muscle becomes inflamed it swells and osmotic pressure increases, causing pain and soreness (Maim, 2001).

Pro-inflammatory cytokines are commonly used as direct markers of inflammation. The previously mentioned study by Meyer et al. (2001) conducted a WAnT study to test the amount of IL-6 being produced post exercise. The first WAnT involved a 60-second, all-out test. The second test involved the same WAnT followed by eight 10-second intervals. Both conditions produced a significant increase in IL-6, but the increase in the interval condition was about six times as great as the WAnT alone.

If anaerobic interval training stimulates a DOMS response through inflammation and oxidative stress, then one should be able to reduce DOMS by reducing either inflammation or oxidative stress. Theaflavins, found in black tea, have been suggested to reduce both inflammation and oxidative stress (Higdon & Frei, 2003; Frei & Higdon, 2003; Stangl, Lorenz & Stangl, 2006). When tea leaves are fermented to form black tea, polyphenols, specifically catechins, are oxidized forming theaflavins (Stangl, Lorenz, & Stangl, 2006). Most of the antioxidant and anti-inflammatory effects have been examined in regards to disease prevention. There is little information regarding theaflavins' effect on oxidative stress and inflammation in exercise and the DOMS model.

In many studies of disease prevention, theaflavins have been suggested to reduce oxidative stress by acting as antioxidants (Frei & Higdon, 2003). Antioxidants bind to the ROS, thereby inhibiting them from taking electrons from polyunsaturated fats in lipid peroxidation. This is known as a radical-scavenging ability. There is evidence to suggest that highly trained athletes have increased endogenous levels of antioxidants (Jacob & Burri, 1996). However, during increased physical activity the muscles use increased amounts of antioxidants possibly leading to an increased need for antioxidant supplementation even in elite athletes (Jacob & Burri, 1996).

By increasing antioxidants through supplementation, lipid peroxidation and oxidative stress may be reduced in turn reducing DOMS. A review by McKay & Blumberg (2002) concluded that black tea improves plasma antioxidant capacity. They also suggested that this antioxidant's efficacy aided in the reduction of many oxidative stress markers in smokers, diabetics and other human subjects. Sü-Alteiner & Yenice (2000) tested the effects of theaflavins on oxidative stress-induced male rats and found that rats treated with $CCl_4$ and black tea had significantly reduced levels of oxidative stress compared to $CCl_4$ alone. Another study tested the antioxidant effect of theaflavins compared to catechins (a known antioxidant in green tea) in vitro. Both catechins and theaflavins reduced MDA, with theaflavins showing a more significant effect (Leung, Su, Chen, Zhang, Haung, & Chen, 2001). No studies to date have examined the effect of theaflavins on exercise induced oxidative stress, or DOMS.

Along with reducing oxidative stress, theaflavins have shown promise in reducing inflammation. One study examined theaflavins' anti-inflammatory ability in vitro by using cells with heightened IL-8 (a pro-inflammatory chemokine) and TNF-α levels (a pro-inflammatory cytokines). Theaflavin treatment significantly reduced the expression of IL-8 and TNF-α compared to a control (Aneja, Odoms, Denenberg, & Wong, 2004). Haung et al. (2006) observed the outcome of theaflavins applied topically and orally to inflamed mouse ears. Mice ears were treated with 12-O-tetradeconoylphorbol-13-acetate (TPA) to induce inflammation and IL-6 levels. Theaflavin treated mice had significantly reduced inflammation as noted by reduced IL-6 levels, and reduced weight of 6 mm ear punches. Theaflavins appear to reduce the production of pro-inflammatory cytokines such as IL-8, TNF-a, and IL-6. As with oxidative stress, no studies have examined the effect of theaflavins and inflammation in a human exercise model.

Materials and Methods of the Clinical Study
Introduction

The purpose of this study was to examine the impact of supplementing with a theaflavin-enriched black tea extract (BTE) on delayed onset muscle soreness (DOMS), inflammation, oxidative stress, and Cortisol responses to a high-intensity anaerobic exercise protocol. Theaflavins have demonstrated anti-inflammatory properties and there is both in vivo and in vitro evidence that this particular BTE (WG0401; WellGen, New Brunswick, N.J.) influences pro-inflammatory cytokine and COX-2 gene expression. This has potential application for recovery from high-intensity exercise, particularly if using repeated anaerobic intervals. Given the interrelated nature of pro-inflammatory cytokine production, HPA axis activation, and formation of reactive oxygen species (ROS), it was hypothesized that BTE would improve recovery from an acute bout of intense exercise. Additionally, it was predicted that the enhanced recovery and reduced inflammation would positively influence the ratings of DOMS at 24 and 48 hours post-exercise.

Tea Extract

The tea extract administered to the subjects was a black tea extract designated WG0401. This particular BTE contains about 6.9% by weight of theaflavin (TF-1), about 14.4% theaflavin-3-gallate, about 4.6% theaflavin-3'-gallate and about 12.6% theaflavin-3,3'-digallate, as measured by HPLC.

Subjects

A total of 18 college-age males ($M_{age}$=21.3±0.4 yrs; $M_{weight}$=84.3±2.5 kg; $M_{height}$=175.8±2.0 cm) with 1+ years of weight training experience ($M_{experience}$=5.4±0.7 yrs) (at least 3 days per week) completed all stages of data collection. Initially, 24 subjects enrolled in the study. However, one subject was promoted to the starting line-up of the wrestling team and was unable to complete testing. The other 5 subjects withdrew of their own volition due to an inability to tolerate the physical demands of the testing protocol. This study was limited to males in order to control for fluctuations in cytokines and Cortisol that occur during the menstrual cycle. Risks and benefits were explained to the subjects and each of them gave written informed consent prior to participation in the study. At initial enrollment, all athletes self-reported to be free from current injuries limiting their ability to train and complete physiological testing. Additionally, all subjects were asked to refrain from using anti-inflammatory medication or drinking tea during the course of the study. Each subject was screened by a member of the research team prior to commencing with each day of testing in order to assess compliance to supplementation and adherence to the exclusion criteria. Based on self-report and capsule count from each returned bottle, it appears that 100% compliance was achieved with the 18 subjects. Prior to enrollment in the study, a health screening was also completed with each subject in accordance with American College of Sports Medicine (ACSM) exercise testing procedures.

Study Design and Supplementation

A double-blind, crossover design was used for this study. Each subject completed a familiarization session to control for practice effects on the anaerobic test (Barfield et al., 2002) and two separate testing sessions (T1 and T2). During T1 and T2, participants had body composition assessed and blood samples were obtained before, immediately after, and 30- and 60-minutes after a Wingate Anaerobic Test (WAnT) for later analysis of oxidative stress markers (8-iso $PGF_{2a}$ [8-isoprostane], total and oxidized glutathione [TGSH and GSSG]), muscle breakdown (creatine kinase [CK]), Cortisol (CORT), and inflammatory cytokines (interleukin-1b [IL-1b], IL-2, IL-4, IL-6, IL-10, IL-12p40, and IFN-y). Additionally, capillary blood samples were analyzed during each test in order to assess blood lactate accumulation and recovery. Participants were asked to rate perceived muscle soreness at 24 and 48 hours post. Subjects were required to refrain from training for 24 hours prior to each test and to refrain from lower body training for at least 24 hours post. Additionally, each subject was tested at the same time of day for each test to control for diurnal variations. Participants were instructed to continue with their normal exercise training during the study.

Following the familiarization session, which included health screening, body composition analysis, and an initial WAnT plus one interval, the subjects were randomly assigned to order of administration of the theaflavin-enriched black tea extract (BTE) (WG0401; WellGen, New Brunswick, N.J.) and a placebo (PLA). The sponsoring company randomly generated the order of administration for each subject. Following this, bottles of the BTE and PLA were provided in a blinded fashion by WellGen, Inc. with a decoding list secured from the investigators until the completion of all assays. Un-blinding occurred at the completion of data processing in order to facilitate data entry. All subjects acknowledged receipt of each bottle and the bottles were returned following each phase of the study to allow for a count of the remaining capsules.

The BTE used in the study contains at least 40% theaflavins, including theaflavin (TF-1), theaflavin-3-gallate (TF-3-G), theaflavin-3'-gallate (TF-3'-G), and theaflavin-3,3'-digallate (TF-3,3'-diG). It also contains approximately 30% catechins and total polyphenols exceeding 95%. In previously conducted clinical trials, there have been no reported side effects or adverse reactions and BTE has a Generally Recognized as Safe (GRAS) US FDA designation. Subjects were instructed to take two capsules in the morning and two in the early afternoon. Each 2-capsule serving of the experimental product contains ~440 mg BTE and is standardized for 175 mg TF. Placebo was matched for appearance.

The initial supplement phase commenced 2-3 days following the familiarization session inorder to allow residual muscle soreness and muscle damage to subside. Subjects consumed the BTE or placebo (PLA) for 9 days. T1 occurred on day 7 and administration continued for 2 more days during the assessment of DOMS. Each subject then underwent a 5-day washout before beginning the 9-day administration period of whichever product they did not receive in the initial supplementation phase. As with the first phase, T2 occurred on day 7 of the second phase and administration continued for an additional 2 days during the assessment of DOMS. The timeline was as follows: Day 1, familiarization; Days 3-11, supplement phase 1 (testing on day 9); Days 12-16, washout phase; Days 17-25, supplement phase 2 (testing on day 23). In order to keep the subjects blind to the condition order, the pills were administered in generic, unlabeled bottles identified only with letters or numbers (numbers for phase 1, letters for phase 2, regardless of the contents) corresponding to their subject ID. To ensure the actual doses of PLA and BTE ingested, subjects were asked to return pill containers containing any placebo/supplement that was not taken. Based on the return, 100% compliance was achieved. A 3-day dietary recall log was used for each subject prior to each Trial and analyzed using commercially available dietary analysis software (FoodWorks, Xyris Software) to assess dietary changes from T1 to T2. Analyses indicated no differences.

Exercise Test Procedures

For each testing day, all subjects reported to the Rutgers University Human Performance Laboratory. Subjects were asked to arrive for testing normally hydrated, have eaten a high carbohydrate meal 2 hours prior, and to refrain from ingesting substances that could affect normal physiological functioning (i.e., tea, coffee, alcohol, nicotine). Satisfaction of these criteria was confirmed prior to commencing with testing. At each test, body composition was assessed using air displacement plethysmography (i.e., BODPOD, Life Measurement, Inc., Concord, Calif.) in order to track lean mass changes that could impact power output. Following this, each athlete rested in a supine position for 10 minutes before commencing with the pretest blood draw. Blood samples were also obtained immediately following completion of the exercise test and at 30 and 60 min post-test with the subject in a supine position.

Subjects performed the WAnT during each testing day on a Monark 894E Anaerobic Test Ergometer (Monark Exercise AB, Sweden). The load was set according to each subject's weight (Üçok et al, 2005). The test was a 30-second WAnT followed by 5 minutes of rest and then eight 10-second intervals of all-out cycling. Each interval was separated by 2 minutes of rest. The resistance for the WAnT and intervals was set at 0.10 kp/kg body weight. Heart rate was continuously monitored using a Polar S810 HR monitor (Polar Electro Co., Woodbury, N.Y.).

Performance Measures

Capillary blood samples (5 µL) were taken from the fingertip during the baseline resting blood draw and at 0, 5, and 10 min post exercise in order to determine peak blood lactate values and clearance. The Lactate Pro (Arkray, Japan) portable analyzer was used to determine whole blood lactate content. The Lactate Pro has previously demonstrated a coefficient of variation of less than 3%. Peak power during the WAnT was defined as the highest mechanical power output elicited during each 30 s test. Average power was calculated based on the average mechanical power produced during the test. Additionally, mean peak power output and mean average power output were calculated across the WAnT and all 8 intervals.

Body Composition

Percent body fat (% BF) was calculated through a two-stage procedure. First, body volume was measured via air displacement plethysmography using the BOD POD (Life Measurement, Inc., Concord, Calif.), as described in previous literature (Dempster & Aitkens, 1995). Using the BOD POD, the error of body volume reading is roughly 0.02%, which allows for calculation of percent body fat with only 0.01% error (Dempster & Aitkens, 1995). The BOD POD was selected to measure body volume due to its comparable precision to DEXA and hydrostatic weighing in calculating % BF (Wells & Fuller, 2001). Height and weight were recorded in conjunction with body composition assessment.

Biochemical Measures

Before ($t_0$), immediately after ($t_1$), 30 min post ($t_2$), and 60 minutes post ($t_3$) each WAnT/interval session, blood samples were collected via an indwelling cannula inserted into an antecubital vein using a vacutainer system (Becton Dickinson, Rutherford, N.J.). Approximately 10 mL were collected in a serum separator tube and 10 mL in an EDTA coated tube. An additional 3 mL at $t_0$, $t_1$ and $t_3$ were collected in a TEMPUS tube (Applied Biosystems, Foster City, Calif.) and stored at −80° C. for later analysis of COX-2 mRNA (assays pending). After removing a 1 mL aliquot of whole blood for hemoglobin and hematocrit analysis, an additional 300 µL aliquot (2×100 µL for GSSG; 2×50 µL for GSH) was obtained for GSH/GSSG analysis. 1-methyl-2-vinylpyridium (M2VP) was added to the tubes containing samples for GSSG analysis. Plasma for 8-isoprostane assay was obtained by centrifugation of whole blood in the EDTA tubes at 3000×g 10 min at 4° C. with 1 mL aliquots placed in microvials pre-coated with 200-µg of butylatedhydroxytoluene (BHT). The serum separator tubes were left to stand for 30 min to facilitate clotting before being centrifuged at 3500×g for 15 min at 4° C. in order to obtain serum for CK, cytokines, and CORT analysis. Aliquots of blood, serum, and plasma were stored at −80° C. until analysis of the dependent measures. All assays were performed in duplicate.

Total and oxidized glutathione was analyzed using a commercially-available EIA kit (Bioxytech® GSH/GSSG-412, OxisResearch, Portland, Oreg.). Similarly, IL-6 was determined via ELISA using commercial kits (IBL, Hamburg, Germany). Serum CK was analyzed using a CK/NAC kinetic assay (StanBio, Boerne, Tex.). Serum Cortisol was analyzed using RIA (MP Biomedicals, Irvine, Calif.). IL-1b, IL-2, IL-4, IL-10, IL-12p40, and IFN-y were sent out for analysis as a custom Searchlight array by Pierce Biotechnology (Woburn, Mass.).

In order to analyze plasma free 8-iso $PGF_{2\alpha}$, plasma from the EDTA tubes was first purified by diluting the sample in a 1:5 ratio with Eicosanoid Affinity Column Buffer (Cayman Chemical, Ann Arbor, Mich.). A known amount of tritiated 8-iso $PGF_{2\alpha}$ was added prior to purification in order to determine recovery rates. Ethanol was added to the solution and the sample was chilled at 4° C. for 5 min to precipitate proteins, and then centrifuged at 1500×g for 10 min at 4° C. The supernatant was decanted and the remaining ethanol evaporated under a nitrogen stream. The pH was then lowered to 4.0 using dropwise addition of HCl. Samples were then passed through a C-18 affinity column (Cayman Chemical, Ann Arbor, Mich.) previously activated with methanol and UltraPure water. Following addition of the sample, the column was washed with 5 mL UltraPure water followed by 5 mL HPLC grade hexane (Sigma Chemical, St. Louis, Mo.). The sample was then eluted with 5 mL of an ethyl acetate: methanol solution (Cayman Chemical, Ann Arbor, Mich.). The elution solution solvents were evaporated again under nitrogen and the samples were then reconstituted in 450 μL EIA buffer (Cayman Chemical, Ann Arbor, Mich.). For each purified sample, 50 μL was analyzed using a commercially available 8-isoprostane EIA kit (Cayman Chemical, Ann Arbor, Mich.), with each sample assayed in duplicate. Absorbance values were determined with a Spectramax 340 microplate reader (Molecular Devices, Sunnyvale, Calif.) between 405 nm and 420 nm and the raw data corrected using the recovery rates of tritiated $PGF_{2\alpha}$.

Delayed Onset Muscle Soreness

A 10 cm visual analog scale (VAS) was used to determine perceived muscle soreness. The anchors at 0 and 10 cm corresponded to "no soreness" and "too sore to move muscles", respectively. Subjects were asked to perform one squat with hands on hips and then draw a line on the scale corresponding to their level of soreness (Twist E. Eston, 2005). Subjects completed the assessments at 24 and 48 hours post testing at T1 and T2.

Statistical Analysis

Peak power, average peak power, mean power, and average mean power were analyzed using RM ANOVAs. A series of 2×4 (Condition×Time) RM ANOVAs were used to analyze LAC, CORT, CK, GSF:GSSG, 8-iso, and cytokine responses. DOMS responses were analyzed using a 2×2 (Condition×Time) RM ANOVA. For each of the above analyses, simple effects and simple contrasts were used as follow-ups where appropriate. Finally, area under the response curve (AUC) for each biochemical variable was calculated using trapezoidal integration in order to determine total secretion responses. AUC for each variable was then analyzed using individual RM ANOVAs. For each univariate analysis, examination of the Huynh-Feldt (H-F) epsilon for the general model was used to test the assumption of sphericity. If this statistic was greater than 0.75, sphericity was considered to have been met and the unadjusted univariate statistic was used. If epsilon was less than 0.75, a violation of the assumption of sphericity was considered to have occurred and the H-F adjusted statistic was used to determine significance. Given the exploratory nature of the study, significance was set at a <0.10.

Results of the Clinical Study

Performance

Figure 2:
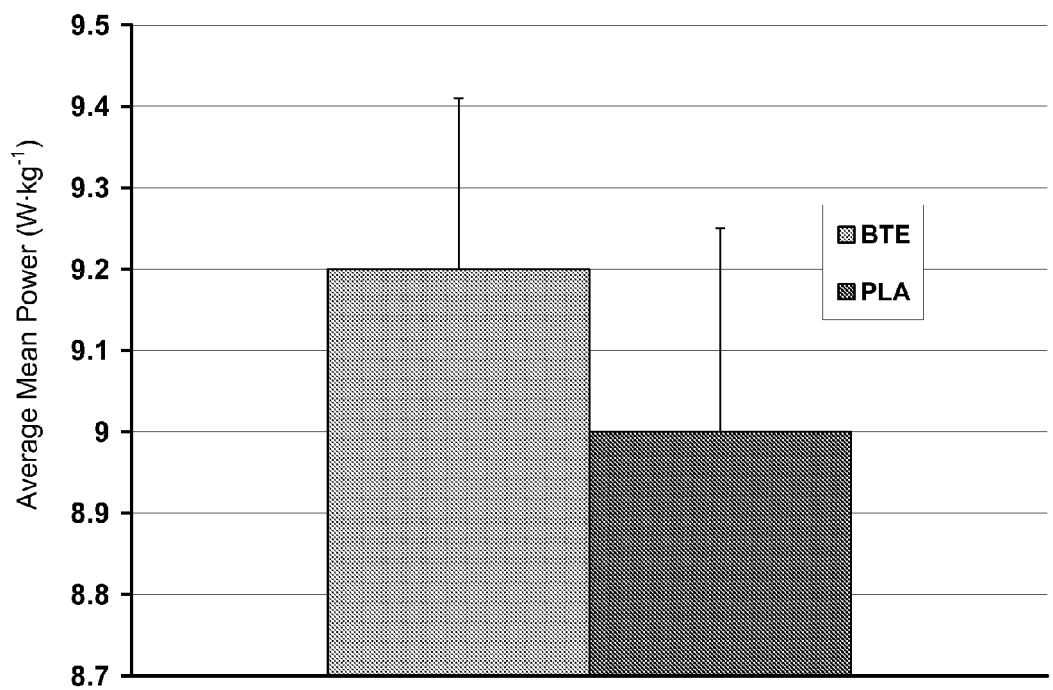
FIG. 2 shows the effects of BTE vs PLA supplementation on average mean power across WAnT and eight 10 s intervals.

There were no significant differences between BTE and PLA on either peak power (P=0.111) or mean power (P=0.395) during the 30 s WAnT. However, when peak power and mean power were averaged across the entire session consisting of the 30 s WAnT and eight 10 s intervals, differences between conditions did emerge. Compared to PLA, BTE produced significantly higher average peak power (BTE=10.85±0.27 W·kg⁻¹; PLA=10.6±0.30 W·kg⁻¹, P=0.013) and higher average mean power (BTE=9.2±0.21 W·kg⁻¹; PLA=9.0±0.25 W·kg⁻¹, P=0.067). See FIGS. 1 and 2.

Delayed Onset Muscle Soreness

Figure 3:
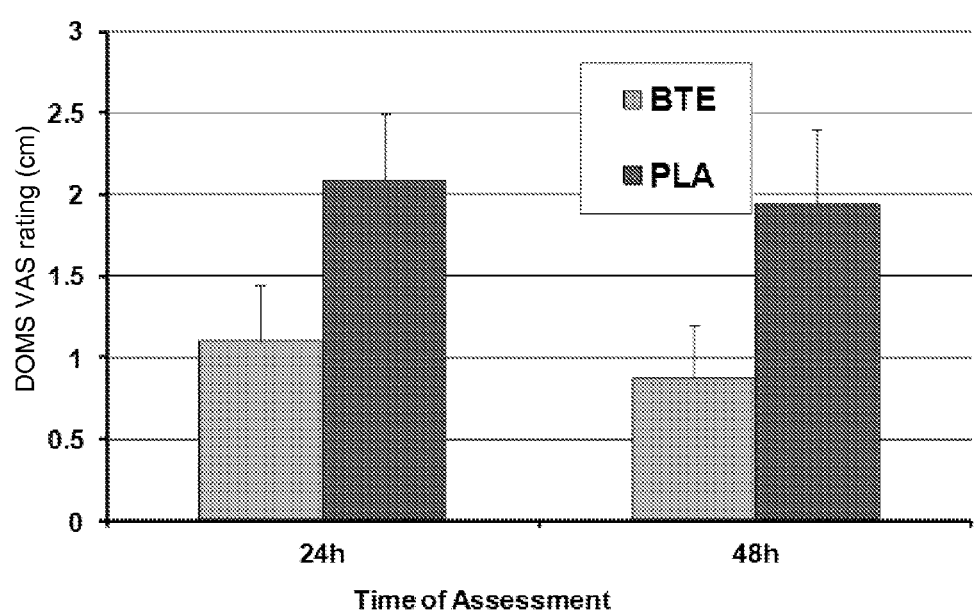
FIG. 3 shows the effects of BTE vs PLA supplementation on delayed onset muscle soreness (DOMS) at 24 h and 48 h post-exercise.

A significant Condition main effect emerged for DOMS (P<0.001). Across the 48 h post-exercise period, BTE produced significantly lower DOMS ratings (24 h=1.12±0.34 cm; 48 h=0.88+0.32 cm) compared to PLA (24 h=2.09±0.40 cm; 48 h=1.94±0.46 cm) (see FIG. 3).

Biochemical & Hormonal Responses

Lactate.

Figure 4:
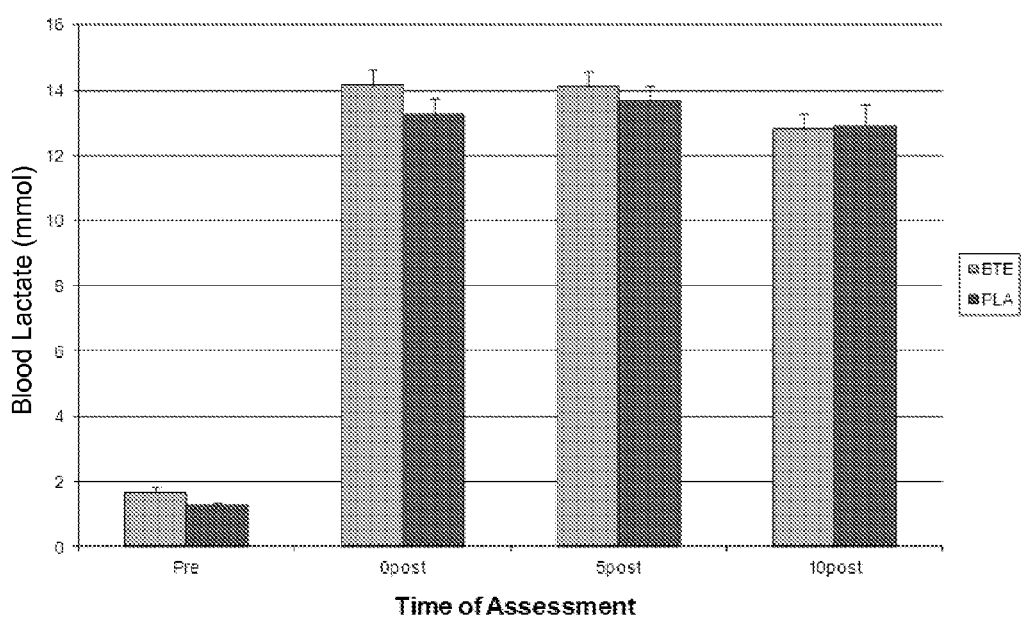
FIG. 4 shows the effects of BTE vs PLA on LAC response following WAnT+intervals.

Significant Time (P<0.001) and Condition (P=0.092) main effects emerged for lactate. Compared to baseline values, both BTE and PLA had significant elevations in LAC at 0, 5, and 10 min post-exercise. The condition main effect appeared to be due to slightly higher LAC concentrations in the BTE condition at 0 and 5 min post. There were no differences in the pattern of LAC response, however (P=0.18) (see FIG. 4).

CK.

Figure 5:
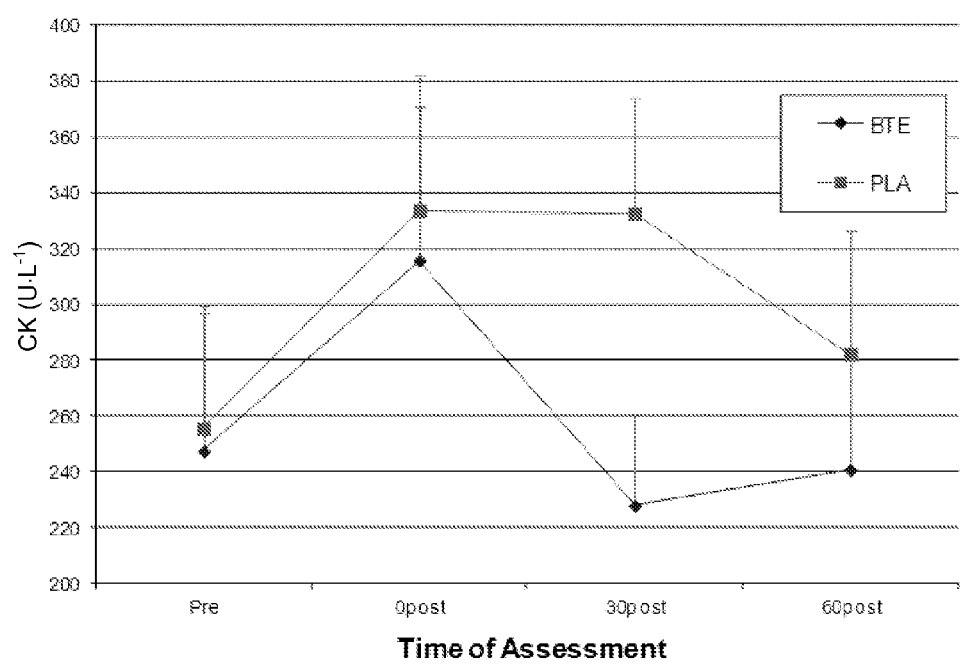
FIG. 5 shows the effects of BTE vs PLA on creatine kinase (CK) response for 60 min following WAnT+intervals.

A significant Time×Condition interaction emerged for CK response (P=0.005). While the WAnT+intervals resulted in significant elevations in CK compared to baseline in both conditions immediately post-exercise (P<0.002), this CK response did not return to baseline until 60 min post in the PLA condition while the BTE condition had recovered to baseline values by 30 min post. Further follow-ups indicated that, compared to PLA, BTE had significantly lower CK at 30 min post (P=0.005) despite similar values immediately post-exercise (P=0.694) (see FIG. 5). AUC analysis was not significant (P=0.219).

Oxidative Stress.

Figure 6:
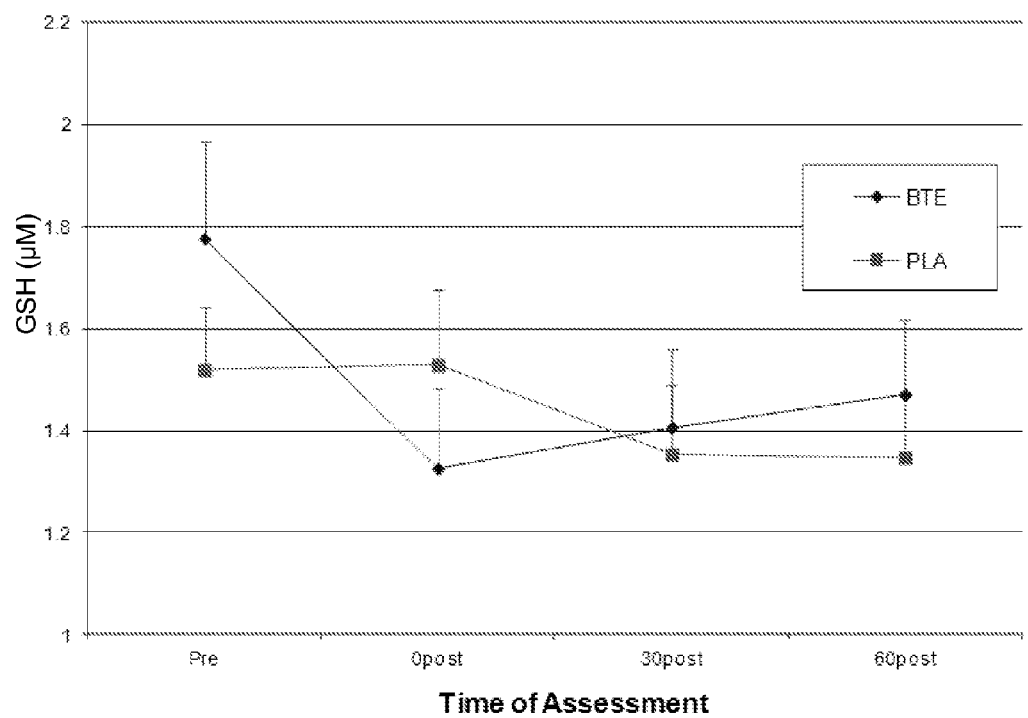
FIG. 6 shows the effects of BTE vs PLA on reduced glutathione (GSH) response for 60 min following WAnT+intervals.
Figure 7:
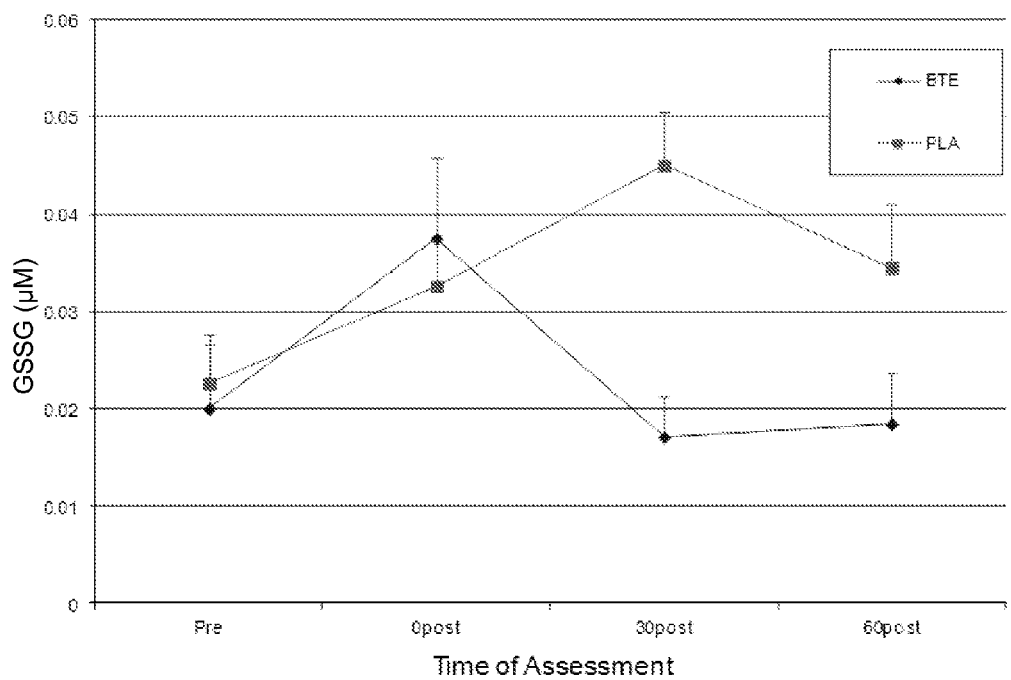
FIG. 7 shows the effects of BTE vs PLA on oxidize glutathione (GSSG) response for 60 min following WAnT+intervals.
Figure 8:
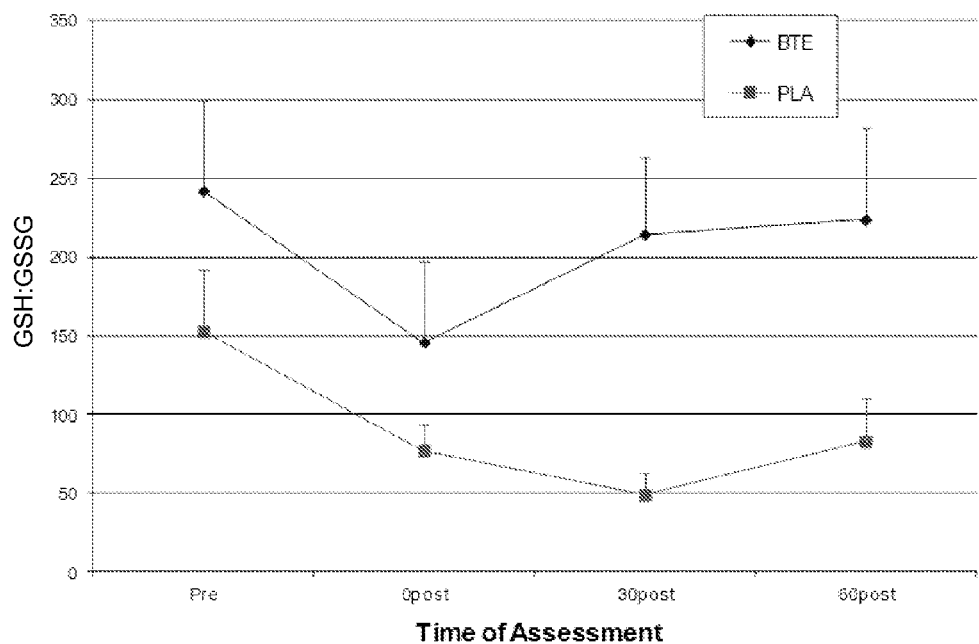
FIG. 8 shows the effects of BTE vs PLA on the GSH:GSSG ratio for 60 min following WAnT+intervals.

A significant Time main effect (P=0.001) and a significant Time×Condition interaction (P=0.056) emerged for GSH (see FIG. 6). The interaction appears to be primarily due to higher baseline GSH in the BTE condition, which is an indicator of antioxidant status. There were no differences in GSH AUC (P=0.94). GSSG also demonstrated a significant Time×Condition interaction (P<0.001) (see FIG. 7). There were equivalent GSSG responses immediately after exercise (0 post), but the oxidative stress was buffered much more quickly by BTE, with significantly lower GSSG in the BTE condition by 30 min post (P<0.001) and persisting through 60 min post (P=0.033). There was a significant difference in AUC between conditions in favor of the BTE condition (P=0.03). Additionally, a significant Time×Condition interaction (P=0.044) emerged for the GSH:GSSG ratio (see FIG. 8). A lower/decreasing ratio indicates greater oxidative stress as GSSG is prevented from reconverting to GSH. In this case, BTE had lower overall oxidative stress at 30 and 60 min post compared to PLA (P<0.02). The AUC analysis for GSH:GSSG was significant (P=0.005), with an overall greater ratio seen for the BTE condition.

Figure 9:
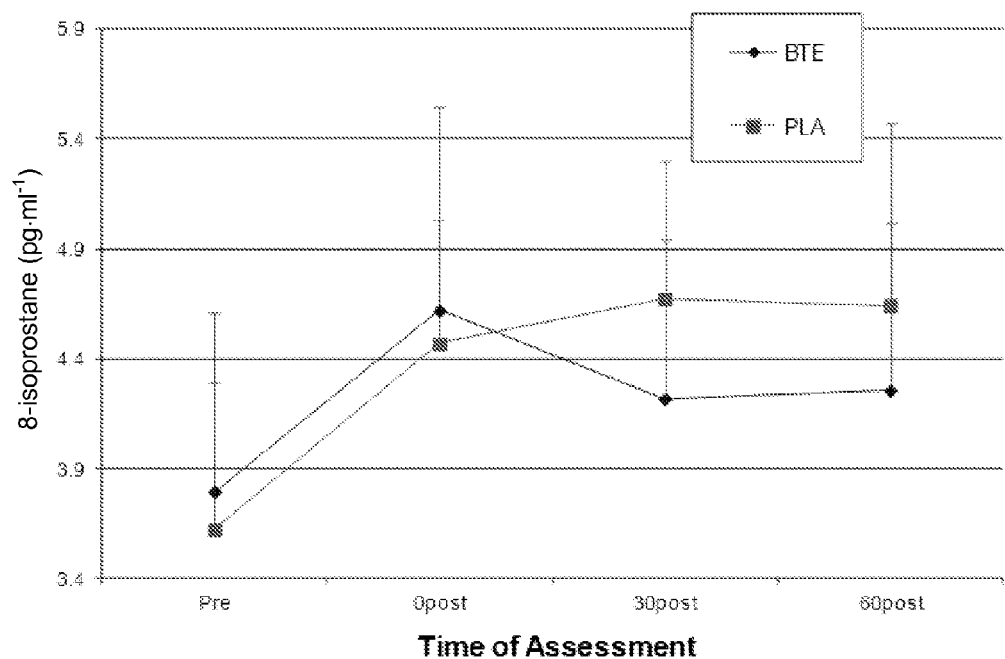
FIG. 9 shows the effects of BTE vs PLA on 8-isoprostane (8-iso) response for 60 min following WAnT+intervals.

There was a significant Time main effect for 8-iso (P=0.067) due to elevated 8-iso secretion following exercise for both conditions (see FIG. 9). Though there was not a significant interaction (P=0.64), AUC analysis revealed significant differences (P=0.097), with lower overall 8-iso secretion in the BTE condition thus indicating lower total oxidative stress.

Cortisol.

Figure 10:
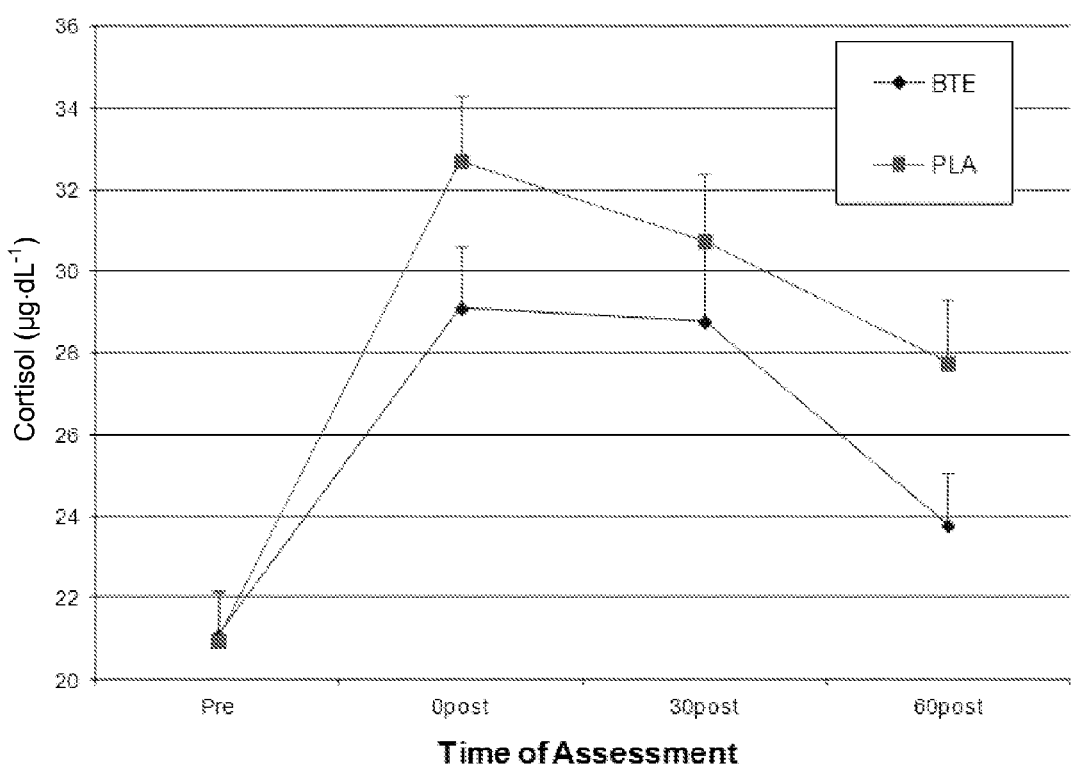
FIG. 10. shows the effects of BTE vs PLA on Cortisol (CORT) secretion for 60 min following WAnT+intervals.
Figure 11:
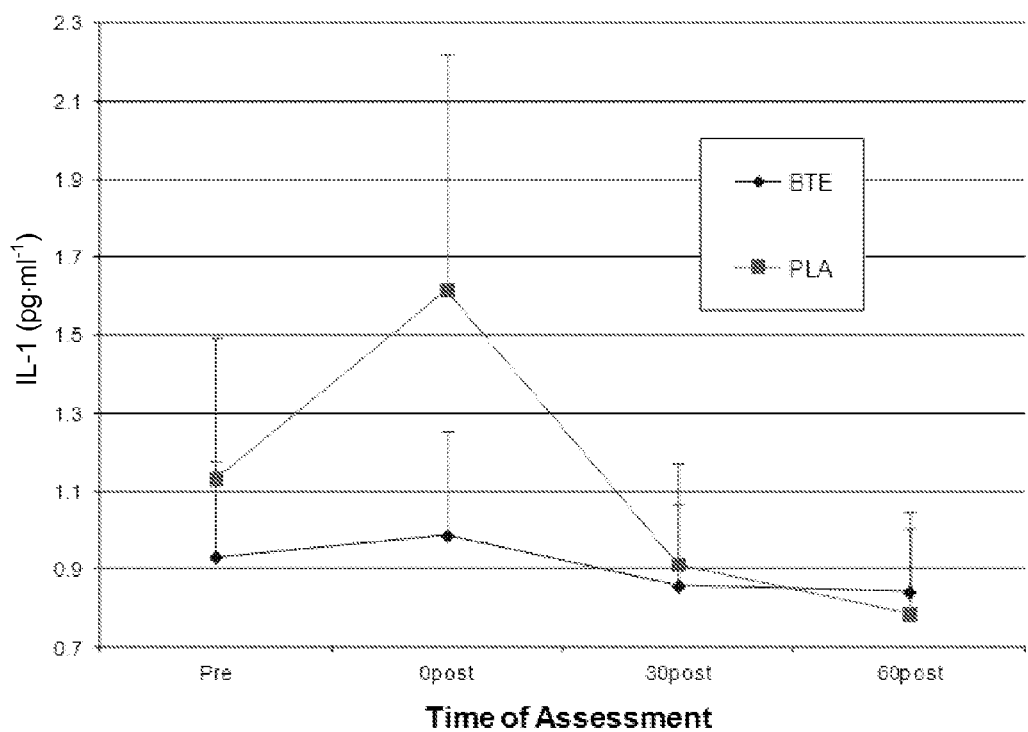
FIG. 11 shows the effects of BTE vs PLA on interleukin-1 (IL-1) response for 60 min following WAnT+intervals.
Figure 12:
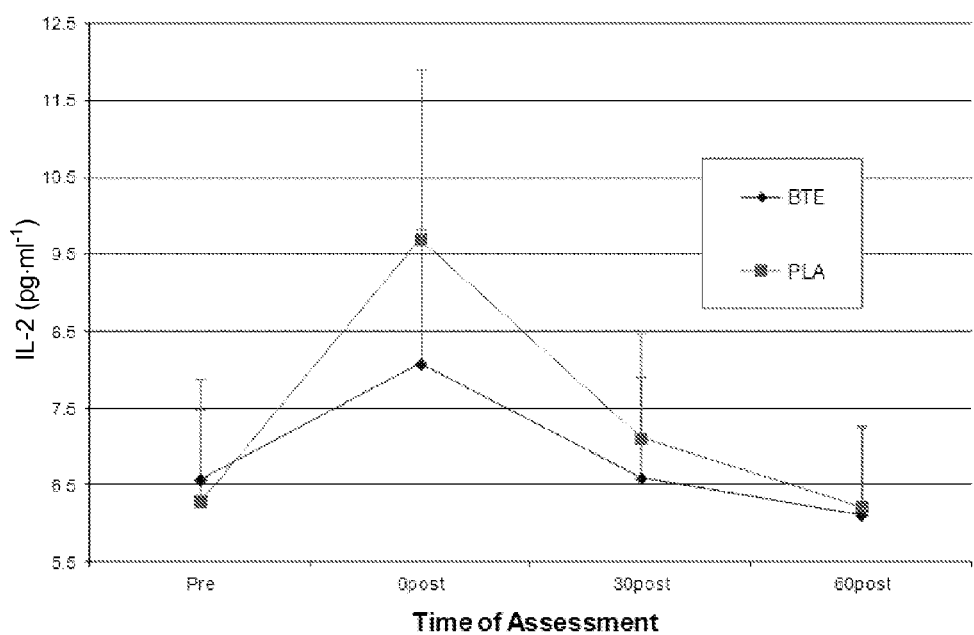
FIG. 12 shows the effects of BTE vs PLA on interleukin-2 (IL-2) response for 60 min following WAnT+intervals.
Figure 13:
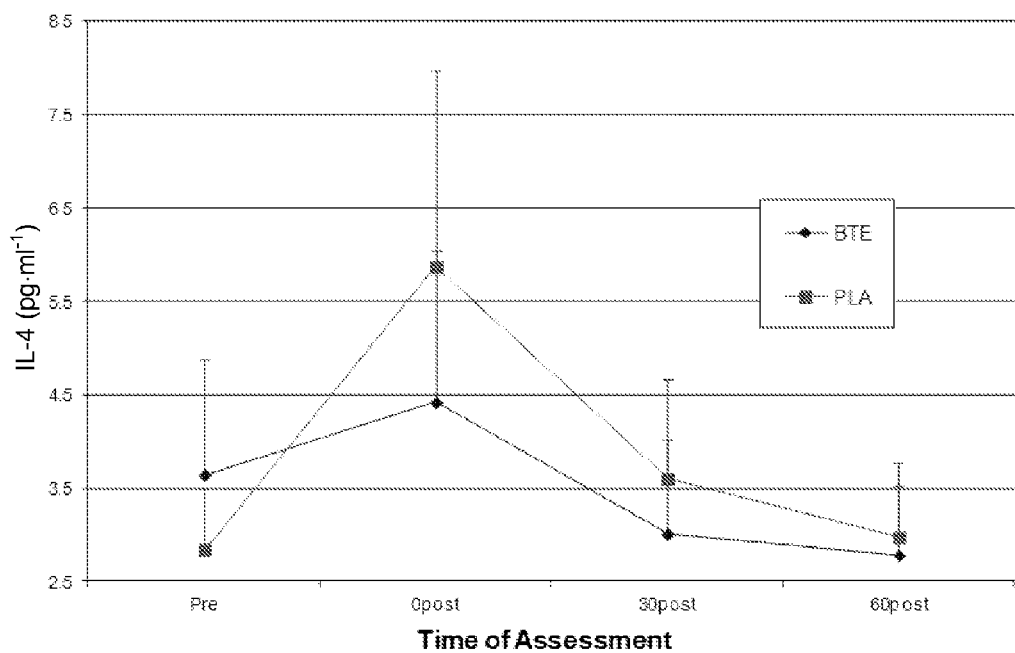
FIG. 13 shows the effects of BTE vs PLA on interleukin-4 (IL-4) response for 60 min following WAnT+intervals.
Figure 14:
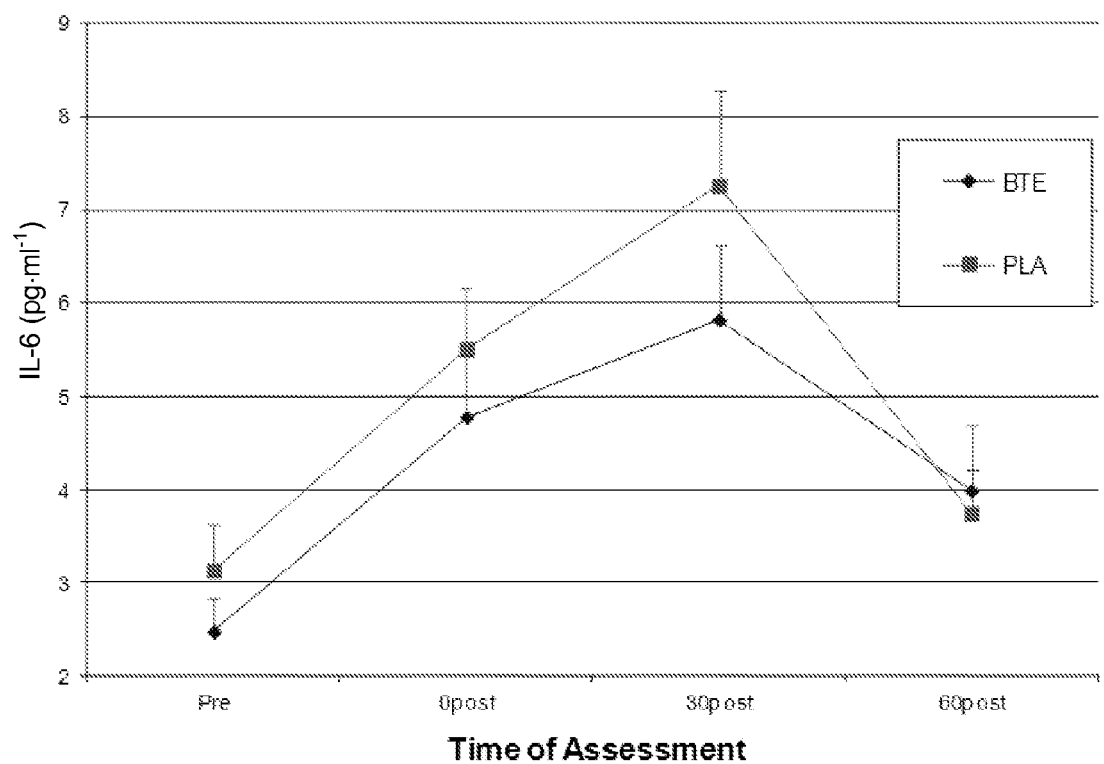
FIG. 14 shows the effects of BTE vs PLA on interleukin-6 (IL-6) response for 60 min following WAnT+intervals.
Figure 15:
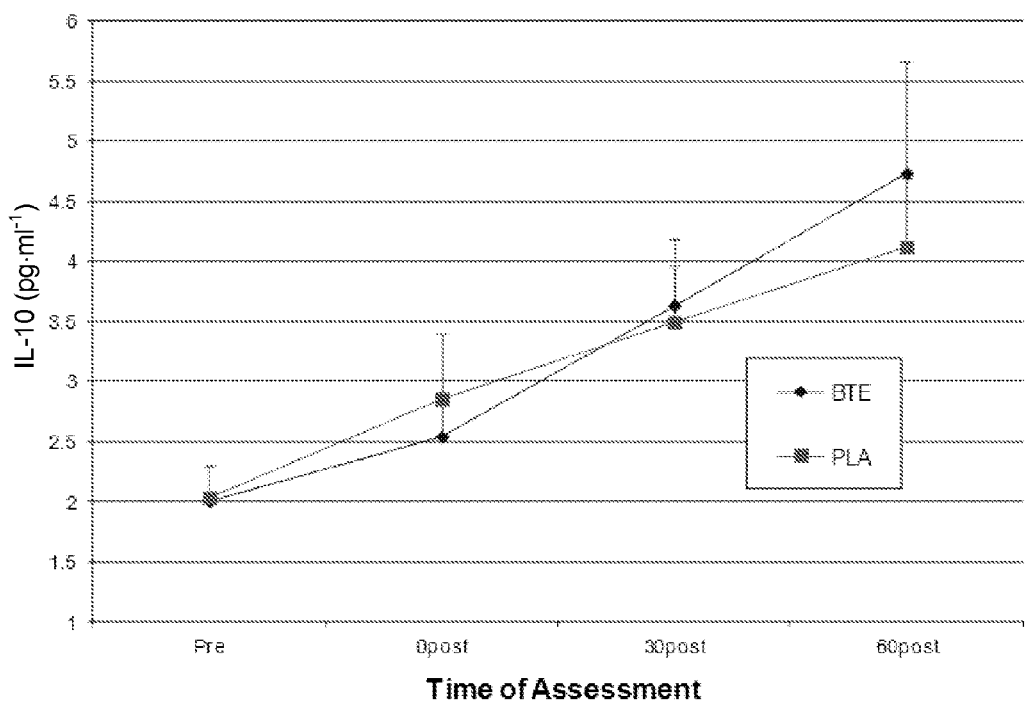
FIG. 15 shows the effects of BTE vs PLA on interleukin-10 (IL-10) response for 60 min following WAnT+intervals.
Figure 16:
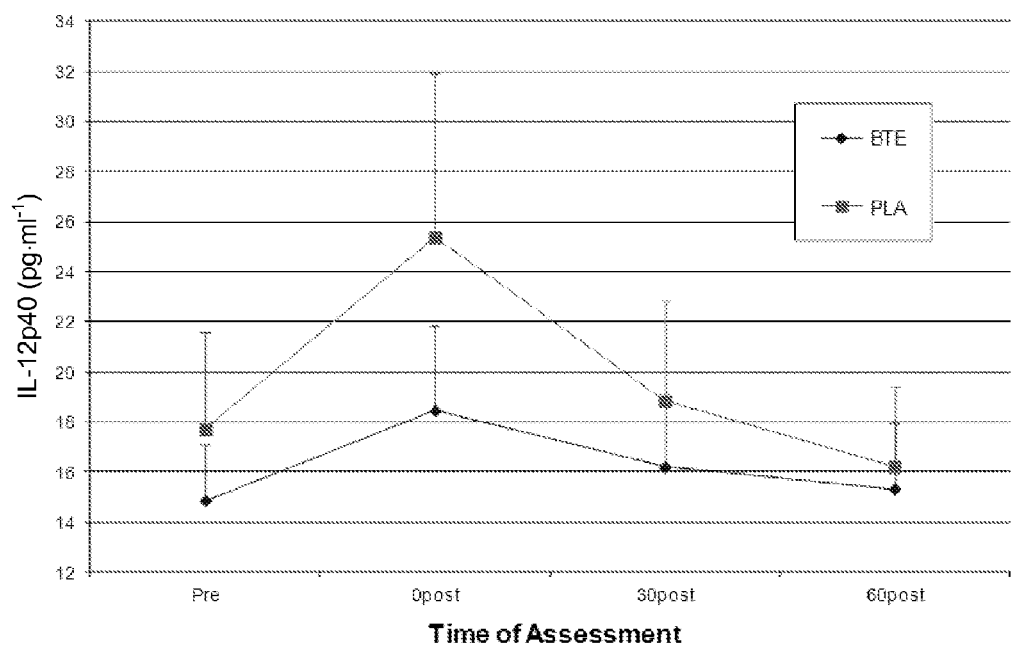
FIG. 16 shows the effects of BTE vs PLA on interleukin-12p40 (IL-12p40) response for 60 min following WAnT+intervals.
Figure 17:
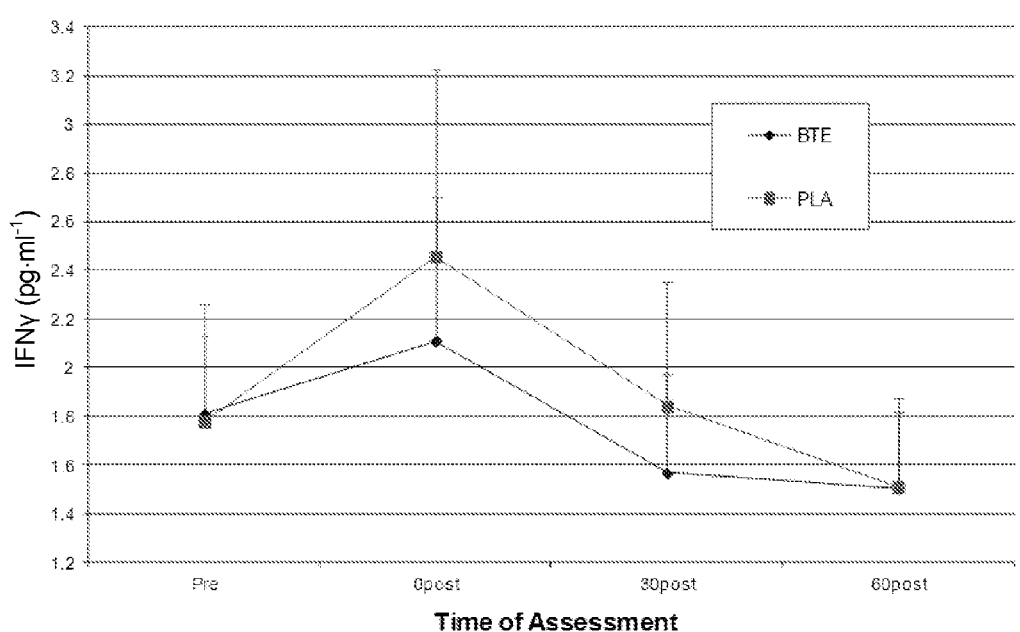
FIG. 17 shows the effects of BTE vs PLA on IFNy response for 60 min following WAnT+intervals.

Significant Time (P<0.001) and Condition (P=0.09) main effects emerged for CORT secretion. Though both conditions produced elevated CORT values post-exercise, the BTE condition had lower overall CORT secretion. The Time×Condition interaction approached significance (P=0.11). It appears that HPA recovery is more pronounced in BTE or that HPA activation was not as pronounced (see FIG. 10). AUC analysis was significant (P=0.098) indicating lower total CORT secretion over the duration of recovery.

Cytokines.

Significant Time main effects emerged for IL-2 (P=0.003), IL-4 (P=0.032), IL-6 (P<0.001), IL-10 (P<0.001), IL-12p40 (P=0.03), and IFNy (P=0.021). The Time main effects for IL-1 approached significance (P=0.13). For all of the cytokines, there were increases across conditions immediately following exercise. However, graphic trends suggest that these responses were more pronounced for the PLA condition in most cases (see FIGS. 11-17), particularly for IL-1, IL-4, IL-6, and IL-12p40. The Condition main effect for IL-12p40 approached significance (P=0.106).

AUC analyses indicated significantly greater total secretion of IL-4 (P=0.086) and IL-12p40 (P=0.098) in PLA compared to BTE. Overall, the cytokine analyses and graphic trends present a cohesive picture of superiority of BTE over PLA for blunting the inflammatory response or for speeding recovery from the inflammation resulting from the high-intensity anaerobic exercise protocol used in this study.

Example 2

Using the extract disclosed in Example 1, one can treat or prevent chronic heart failure. To perform this treatment, a subject takes the extract of Example 1 and subsequently exercises. The extract will decrease the effects of delayed onset muscle soreness and exercise-induced acute inflammation experienced by the subject, and will decrease recovery time after the exercise session. This will permit the subject to exercise more frequently with less soreness so as to stimulate cardiac health in the subject and thereby treat or prevent chronic heart failure in the subject.

Example 3

Using the extract disclosed in Example 1, one can enhance a positive response to physical therapy. To enhance a response to physical therapy, a subject takes the extract of Example 1 and subsequently performs physical therapy. The extract will decrease the effects of delayed onset muscle soreness and exercise-induced acute inflammation experienced by the subject, and will decrease recovery time after the physical therapy session. This will permit the subject to perform physical therapy more frequently with less soreness so as to enhance the subject's positive response to physical therapy.

Example 4

Using the extract disclosed in Example 1, one can maintain one's flexibility after exercising. To maintain flexibility, a subject takes the extract of Example 1 and subsequently exercises. The extract will decrease the effects of delayed onset muscle soreness and exercise-induced acute inflammation experienced by the subject, thereby allowing the subject to maintain flexibility after the exercise session.

Example 5

Using the methods disclosed in Examples 1-4 above, the same results can be achieved by using an ethyl acetate extract of tea instead of the black tea extract disclosed in Example 1. A suitable tea extract is made by fermenting green tea to form a mixture of theaflavin, theaflavin-3-gallate, theaflavin-3'-gallate and theaflavin-3,3'-digallate, which theaflavins are then extracted from the mixture by contacting them with organic solvent, such as ethyl acetate. In one instance the mixture of theaflavins is greater than 95% pure and contains between about 40% and about 50% theaflavin, between about 15% and about 25% of theaflavin-3-gallate, between about 10% and about 14% theaflavin-3'-gallate and between about 15% and about 25% of theaflavin-3,3'-digallate. In another instance, the mixture of theaflavins is comprised of about 47% theaflavin, about 19% of theaflavin-3-gallate, about 14% theaflavin-3'-gallate and about 20% of theaflavin-3,3'-digallate. It has been established that these extracts will provide the same benefits described in Examples 1-4 when they are administered to a subject in an effective amount.

Example 6

Using the methods disclosed in Examples 1-4 above, the same results can be achieved by using an ethyl acetate extract of black tea instead of the black tea extract disclosed in Example 1. A suitable tea extract is made by extracting theaflavins from black tea with ethyl acetate to form a mixture of theaflavin-3-gallate and theaflavin 3'-gallate. In one instance, theaflavin-3-gallate and theaflavin-3'-gallate are present in a total concentration of up to 5% of the composition. In another instance, the theaflavin-3-gallate and theaflavin-3'-gallate are present in a total concentration of between 50 µM and 100 µM in the composition. It has been established that these extracts will provide the same benefits described in Examples 1-4 when they are administered to a subject in an effective amount.

Example 7

Using the methods disclosed in Examples 1-4 above, the same results can be achieved by administering a compound containing theaflavins synthesized from green tea polyphenols instead of the black tea extract disclosed in Example 1. A suitable compound is made by subjecting specific green tea polyphenols to enzymatic oxidation methods to independently synthesize theaflavin, theaflavin-3-gallate, theaflavin-3'-gallate, and theaflavin-3,3'-digallate. It has been established that this compound will provide the same benefits described in Examples 1-4 when it is administered to a subject in an effective amount.

Example 8

Using the methods disclosed in Examples 1-4 above, the same results can be achieved by administering a black tea extract made from a tea cream instead of the black tea extract disclosed in Example 1. A suitable compound is made by extracting black tea with water, concentrating the solution into a tea cream, and extracting theaflavins from the solution with an organic liquid. In one instance, the mixture contains about 21.37% by weight of theaflavins. In another instance, the mixture contains about 3.55% theaflavin, about 5.95% theaflavin-3-gallate, about 3.75% theaflavin-3-gallate, and about 8.14% theaflavin-3,3'-digallate. It has been established that this black tea extract will provide the same benefits described in Examples 1-4 when it is administered to a subject in an effective amount.

Example 9

Using the methods disclosed in Examples 1-4 above, the same results can be achieved by administering an ethanol extract of tea instead of the black tea extract disclosed in Example 1. A suitable tea extract is made by fermenting green tea and extracting theaflavins from the mixture with ethanol. It has been established that this black tea extract will provide the same benefits described in Examples 1-4 when it is administered to a subject in an effective amount.

Example 10

Using the extract disclosed in Example 1, one can enhance athletic exercise power and performance. To enhance athletic exercise power and performance, a subject takes the extract of Example 1 and subsequently exercises. The extract will decrease the effects of delayed onset muscle soreness and exercise-induced acute inflammation experienced by the subject, thereby allowing the subject to maintain enhanced power and performance during exercise.

A method for enhancing athletic exercise power and performance of a subject which comprises administering to the subject a composition comprising a physiologically acceptable carrier or excipient and an extract of tea, wherein the extract comprises at least 10% by weight of total theaflavin and wherein the composition is administered in an amount effective to enhance the subject's athletic power and performance.

REFERENCES

1. Aneja, R., Odoms, K., Denenberg, A. G., & Wong, H. R. (2004). Theaflavin, a black tea extract, is a novel anti-inflammatory compound. *Critical Care Medical*, 32, 2097-2103.
2. Baker, J. S., Bailey, D. M., Hullin, D., Young, I., Davies, B. (2004). Metabolic implications of resistive force selection for oxidative stress and markers of muscle damage during 30 s of high-intensity exercise. *European Journal of Applied Physiology*, 92, 321-327.
3. Basu, S. (2003). Isoprostane: novel bioactive products of lipid peroxidation. *Free Radical Research*, 38, 105-122.
4. Bloomer, R. J., Goldfarb, A. H., McKenzie, M. J., You, T., & Nguyen, L. (2004). Effects of antioxidant therapy in women exposed to eccentric exercise. *International Journal of Sport Nutrition* and *Exercise Metabolism*, 14, 377-388.
5. Childs, A., Jacobs, C., Kaminski, T., Halliwell, B., Leeuwenburgh, C. (2001). Supplementation with vitamin C and N-acetyl-cysteine increases oxidative stress in humans after an acute muscle injury induced by eccentric exercise. *Free Radical Biology & Medicine*, 31, 745-753.
6. Clarkson, P. M., & Thompson, H. S. (2000). Antioxidants: what role do they play in physical activity and health? *American Journal of Clinical Nutrition*, 72(Suppl.), 637-646.
7. Clarkson, P. M., & Hubal, M. J. (2002). Exercise-induced muscle damage in humans. *American Journal of Physiological* and *Medical Rehabilitation*, 8(Suppl.), 52-69.
8. Dudly, G. A., (1999). Muscle pain prophylaxis. *Inflammopharmacology*, 7(3):249-53.
9. Feasson, L., Stockholm, D., Freyssenet, D., Richard, I., Duguez, S., Beckmann, J. S., & Denis, C. (2002). Molecular adaptations of neuromuscular disease-associated proteins in response to eccentric exercise in human skeletal muscle. *The Journal of Physiology*, 543, 297-306.
10. Frei, B., & Higdon, J. V. (2003). Antioxidant Activity of Tea Polyphenols In Vivo: Evidence from Animal Studies. *Journal of Nutrition*, 133, (Suppl.) 3275-3284.
11. Goldfarb, A. H., Bloomer, R. J., & McKenzie, M. J. (2005). Combined antioxidant treatment effects on blood oxidative stress after eccentric exercise. *Medicine & Science in Sports & Exercise*, 37, 234-239.
12. Groussard, C, Rannou-Bekono, F., Machefer, G., Chevanne, M., Vincent, S., Sergent, O., et al. (2003). Changes in blood lipid peroxidation markers and antioxidants after a single spring anaerobic exercise. *European Journal of Applied Physiology*, 89, 14-20.
13. Guevas, M. J., Almar, M., Garcia-Glez, J., Garcia-Lopez, D., De Paz, J. A., Alvear Órdenes, I., & Gonzalez-Gallego, J. (2005). Changes in oxidative stress markers and NF-kB activation induced by sprint exercise. *Free Radical Research*, 39, 431-439.
14. Haung M. T., Liu, Y., Ramji, D., Lo, C. Y., Ghai, G., Dushenkov, S., & Ho, C. T. (2006). Inhibitory effects of black tea theaflavin derivatives on 12-O-tetradecanoylphorbol-12-acetate-induced inflammation and arachidonic acid metabolism in mouse ears. *Molecular Nutrition and Food Research*, 50, 115-122.
15. Higdon, J. V., & Frei, B. (2003). Tea catechins and polyphenols: Health effects, metabolism, and antioxidant functions. *Critical Reviews in Food Science* and *Nutrition*, 43, 89-143.
16. Jacob, R. A., & Burri, B. J. (1996). Oxidative damage and defense. *American Journal of Clinical Nutrition*, 63(Suppl.), 985-990.
17. Lee, J., Goldfarb, A. H., Rescino, M. H., Hedge, S., Patrick, S., & Apperson, K. (2002). Eccentric exercise effect on blood oxidative-stress markers and delayed onset of muscle soreness. *Medicine & Science in Sports & Exercise*, 34, 443-448.
18. Leung, L. K., Su, Y., Chen, R., Zhang, A., Haung, U., & Chen, Y., Z. (2001). Theaflavins in black tea and catechins in green tea are equally effective antioxidants. *Journal of Nutrition*, 131, 2248-2251.
19. Malm, C. (2001). Exercise-induced muscle damage and inflammation: fact or fiction? *Acta Physiologica Scandinavia*, 171, 233-239.
20. MacIntyre, D. L., Sorichter, S., Mair, J., Berg, A., & McKenzie, D. C. (2001) Markers of inflammation and myofibrillar proteins following eccentric exercise in humans. *European Journal of Applied Phyiology*, 84, 180-186.
21. McAnulty, S., McAnulty, L., Nieman, D., Morrow, J., Dumke, C., & Henson, D. (2007). Effect of NSAID on muscle injury and oxidative stress. *International Journal Sports Medicine*, 28(11):909-15.
22. McArdle, W. D., Katch, F. I., & Katch, W. L (2001). *Exercise Physiology: Energy, Nutrition*, and *Human Performance* (5$^1$ ed.). Baltimore: Lippincott Williams & Williams.
23. McBride, J. M., Kraemer, W. J., Triplett McBride, T., & Sebastianelli, W. (1998). Effect of resistance exercise on free radical production. *Medicine & Science in Sports & Exercise*, 30, 67-72.
24. McKay, D. L., & Blumberg, J. B. (2002). The role of tea in human health: an update. *Journal of the American College of Nutrition*, 21, 1-13.
25. Meyer, T., Gabriel, H. H. W. G, Ratz, M., Muller, H. J., & Kindermann, W. (2001). Anaerobic exercise induces moderate acute phase response. *Medicine & Science in Sports & Exercise*, 33, 549-555.
26. Nosaka, K., & Clarkson, P. M. (1996). Changes in indicators of inflammation after eccentric exercise of the elbow flexors. *Medicine and Science in Sports and Exercise*, 28, 953-961.
27. Reid, M. B., & Li, Y. P. (2001). Cytokines and oxidative signaling in skeletal muscle. Acta Physiologica Scandinavia, 171, 225-232.
28. Rice, T. L., Chantler, I., & Loram, L. C. (2008). Neutralisation of muscle tumour necrosis factor alpha does not attenuate exercise-induced muscle pain but does improve muscle strength in healthy male volunteers. *Br J Sports Med.* 42(9):758-62.
29. Stangl, V., Lorenz, M., & Stangl, K. (2006). Review: The role of tea and tea flavonoids in cardiovascular health. *Molecular Nutrition and Food Research*, 50, 218-228.
30. Stone, M. B., Merrick, M. A., Ingersoll, C. D., & Edwards, J. E. (2002). Preliminary comparison of bromelain and Ibuprofen for delayed onset muscle soreness management. *Clin J Sport Med.* 12(6):373-8.
31. Sur-Alteiner, D., & Yenice, B. (2000). Effect of black tea on lipid peroxidation in carbon tetrachloride treated male rats. *Drug metabolism and Drug Interactions* 16, 123-128.

32. Tidball, J. G. (2005). Inflammatory processes in muscle injury and repair. *American Journal of Physiological Regulatory, Integrative*, and *Comparative Physiology, 288*, 345-353.
33. Tomita, M., Irwin, K. I., Xie, Z. J., & Santoro, T. J. (2002). Tea pigments inhibit the production of type 1 (THI) and type 2 (TH2) helper T cell cytokines in CD4+. T cells. *Phytotherapy Research, 16*, 36-42.
34. Twist, C, & Eston, R. (2005). The Effects of exercise-induced muscle damage on maximal intensity intermittent exercise performance. *European Journal of Applied Physiology, 94*, 652-658.
35. Vassilakopoulos, T., Karatza, M. H., Katsaounou, P. Kollintza, A., Zakynthinos, S., & Roussos, C. (2003). Antioxidants attenuate the plasma cytokine response to exercise in humans. *Journal of Applied Physiology, 94*, 1025-1032.
36. Willoughby, D. S., McFarlin, B., & Bois, C. (2003). Interleukin-6 expression after repeated bouts of eccentric exercise. *International Journal of Sports Medicine, 24*, 15-21.

What is claimed is:

1. A method for treating a human suffering from exercise-induced, acute inflammation from muscle cell degradation in the human consisting essentially of administering to said human a therapeutically effective amount of an extract of black tea or oolong tea effective to treat said human suffering from exercise-induced, acute inflammation from muscle cell degradation, wherein the extract is extracted with a solvent selected from the group consisting of an ethyl acetate extract, an ethanol extract, and a super critical $CO_2$ extract which treats the human suffering from exercise-induced, acute inflammation from muscle cell degradation.

2. The method of claim 1, wherein the extract contains theaflavin, theaflavin-3-gallate, theaflavin-3'-gallate, and theaflavin-3,3'-digallate.

3. The method of claim 2, wherein the extract contains at least 20% by weight of total theaflavins.

4. The method claim 2, wherein the extract is an ethyl acetate extract.

5. The method of claim 2, wherein the amount effective to treat said human is a dosage of about 50 mg to about 2600 mg of total theaflavins per day.

6. The method of claim 5, wherein the amount effective to treat said human is a dosage of about 300 mg to about 1000 mg of total theaflavins per day.

7. The method of claim 6, wherein the amount is about 175 mg of total theaflavins and is administered twice per day.

* * * * *